(12) United States Patent
Ricotta, Jr. et al.

(10) Patent No.: US 12,259,994 B2
(45) Date of Patent: *Mar. 25, 2025

(54) SYSTEMS AND METHODS FOR ACCESSING DIGITAL ASSETS IN A BLOCKCHAIN USING GLOBAL CONSENT CONTRACTS

(71) Applicant: BurstiQ, Inc., Englewood, CO (US)

(72) Inventors: Frank J. Ricotta, Jr., Colorado Springs, CO (US); Brian Jackson, Parker, CO (US); Tyson Henry, Castle Rock, CO (US); Amber Hartley, Lakewood, CO (US)

(73) Assignee: BurstiQ, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,781

(22) Filed: Apr. 8, 2024

(65) Prior Publication Data

US 2025/0021682 A1    Jan. 16, 2025

Related U.S. Application Data

(60) Continuation of application No. 18/318,207, filed on May 16, 2023, now Pat. No. 11,954,222, which is a
(Continued)

(51) Int. Cl.
*G06F 21/62* (2013.01)
*G06F 16/23* (2019.01)
(Continued)

(52) U.S. Cl.
CPC ...... *G06F 21/6218* (2013.01); *G06F 16/2379* (2019.01); *G06F 21/602* (2013.01);
(Continued)

(58) Field of Classification Search
CPC .............. G06F 16/2379; G06F 21/602; G06F 21/6218; G06Q 10/10; G06Q 30/0185;
(Continued)

(56) References Cited

U.S. PATENT DOCUMENTS

| | | | |
|---|---|---|---|
| 11,228,810 B1 * | 1/2022 | Arazi | H04N 21/6582 |
| 2004/0205358 A1 * | 10/2004 | Erickson | H04L 63/126 |
| | | | 726/33 |

(Continued)

*Primary Examiner* — Gary S Gracia
(74) *Attorney, Agent, or Firm* — Maynard Nexsen PC; Michael Henson

(57) ABSTRACT

A consent block is a type of block that may be stored in a blockchain. Each consent block has an owner and may store an owner consent contract, i.e., a smart contract containing owner-specified access rules that determine who may access data assets that are stored in other blocks of the blockchain and owned by the same owner. The consent block may alternatively store a global consent contract containing global access rules that supersede owner-specified access rules. The consent block also stores a hash value determined from the consent contract and a previous hash value of the block immediately preceding the consent block. The consent
(Continued)

contract and the position of the consent block in the blockchain are verifiable from the hash value. Each consent block, once added to the blockchain, becomes part of the immutable record of data stored in the blockchain, and therefore leaves an auditable trail.

7 Claims, 18 Drawing Sheets

Related U.S. Application Data division of application No. 17/001,302, filed on Aug. 24, 2020, now Pat. No. 11,651,096.

(51) Int. Cl.
| | | |
|---|---|---|
| *G06F 21/60* | (2013.01) | |
| *G06Q 10/10* | (2023.01) | |
| *G06Q 30/018* | (2023.01) | |
| *G06Q 50/26* | (2012.01) | |
| *G16H 10/20* | (2018.01) | |
| *G16H 10/60* | (2018.01) | |
| *H04L 9/06* | (2006.01) | |

(52) U.S. Cl.
CPC ......... *G06Q 10/10* (2013.01); *G06Q 30/0185* (2013.01); *G06Q 50/265* (2013.01); *G16H 10/20* (2018.01); *G16H 10/60* (2018.01); *H04L 9/0643* (2013.01)

(58) Field of Classification Search
CPC ...... G06Q 50/265; G16H 10/10; G16H 10/60; H04L 9/0643
See application file for complete search history.

(56) References Cited

U.S. PATENT DOCUMENTS

| | | | |
|---|---|---|---|
| 2017/0116693 A1* | 4/2017 | Rae | G06Q 50/184 |
| 2018/0182052 A1* | 6/2018 | Panagos | G06Q 10/10 |
| 2018/0349990 A1* | 12/2018 | Diriye | G06Q 40/03 |
| 2019/0012466 A1* | 1/2019 | Ricotta | H04L 67/535 |
| 2019/0028277 A1* | 1/2019 | Jayachandran | H04L 9/3247 |
| 2019/0156363 A1* | 5/2019 | Postrel | H04L 67/566 |
| 2019/0188411 A1* | 6/2019 | Kroutik | H04L 9/3297 |
| 2019/0215564 A1* | 7/2019 | Webb | H04N 21/4627 |
| 2019/0238525 A1* | 8/2019 | Padmanabhan | H04L 63/101 |
| 2019/0268140 A1* | 8/2019 | Kandiraju | H04L 9/3239 |
| 2019/0294817 A1* | 9/2019 | Hennebert | H04L 9/0861 |
| 2019/0356471 A1* | 11/2019 | Vaughn | H04L 9/3247 |
| 2020/0117818 A1* | 4/2020 | Latka | H04L 67/1097 |
| 2020/0162473 A1* | 5/2020 | Mercuri | G06Q 20/065 |
| 2020/0250176 A1* | 8/2020 | Padmanabhan | H04L 9/3239 |
| 2020/0250661 A1* | 8/2020 | Padmanabhan | G06Q 20/367 |
| 2020/0250747 A1* | 8/2020 | Padmanabhan | G06Q 20/065 |
| 2020/0252205 A1* | 8/2020 | Padmanabhan | G06F 16/24564 |
| 2020/0258605 A1* | 8/2020 | Blechman | G16H 40/67 |
| 2020/0358801 A1* | 11/2020 | Allouche | H04L 63/123 |
| 2020/0389309 A1* | 12/2020 | Ricotta | H04L 9/32 |
| 2020/0396065 A1* | 12/2020 | Gutierrez-Sheris | H04L 9/3297 |
| 2021/0390196 A1* | 12/2021 | Lavine | H04L 63/102 |
| 2022/0058732 A1* | 2/2022 | Reses | G06Q 20/065 |

* cited by examiner

400

```
consents 4bed39ae399bd1...
for chain_name
when asset.identifier = 15131
until date('2019-12-12T12:43:22-0000')
only attr3, attr4, attr5
```

```
consents 4bed39ae399bd1..., 825763ff373aca...
for chain_name
when asset.identifier = 15131
until date('2019-12-12T12:43:22-0000')
only attr3, attr4, attr5
```

```
consents 'researcher'
for chain_name
when asset.identifier = 15131
until date('2019-12-12T12:43:22-0000')
only attr3, attr4, attr5
```

*FIG. 6*

```
consents global suppress *
for chain_name
when asset.test = 'CBC'
```

SYSTEMS AND METHODS FOR ACCESSING DIGITAL ASSETS IN A BLOCKCHAIN USING GLOBAL CONSENT CONTRACTS

CROSS-REFERENCE TO RELATED APPLICATION(S)

This application is a continuation and claims priority to U.S. application Ser. No. 18/318,207, filed May 16, 2023. U.S. application Ser. No. 18/318,207 is a division of U.S. application Ser. No. 17/001,302, filed Aug. 24, 2020, now U.S. Pat. No. 11,651,096, the disclosure of which is incorporated herein by reference in its entirety.

BACKGROUND

Cloud computing offers convenient storage and access to data, often referred to as Infrastructure as a Service (IaaS) or Platform as a Service (PaaS). However, while such services offer a cost effective and convenient solution to data storage, security and data privacy are of concern, and prevent certain sectors of the business market from using these cloud storage solutions. These concerns are magnified by increasing news of hackers gaining access to personal data and selling it on a black market.

SUMMARY

Over the last decade, new technology has enabled and accelerated movement towards cloud computing. The convergence of digital health innovations, advances in precision medicine, and the acceleration of machine intelligence are expected to usher in a new age in health, one in which everyone has access to the healthcare they need, one that improves the quality of life for everyone, and one in which many diseases will be eliminated.

Data about you (e.g., what you do, how you feel, where you live, what you eat, etc.) is becoming critically important to almost every application and service in the health economy. Consumer products, point-of-care services, and clinical research studies rely on health-related data to understand how to optimize patient care and operations. Health data is required to enable tools such as provider-facing decision support engines, patient engagement applications, wellness coaches, and more. In effect, health data is now the currency driving person-centric health. Corporations want to own this data, researchers need better access to it, and companies are building new solutions every day to collect more of it. As a result, the value of health data is increasing rapidly, and regulatory oversight and policies regarding ownership and control of health data are gaining momentum. The hackers on the dark web know it is valuable too; one in four security breaches are health related, creating a multibillion-dollar black market for health data and a multibillion-dollar economic remediation burden for health providers.

The increasing amount of health data, its critical importance to the industry, and the increasing regulation of its ownership and exchange, are all driving the need for new data management solutions that enable data to be securely owned and shared in a manner that is traceable, compliant with applicable regulations, and revocable. Traditional data management solutions, including both local (i.e., on-premise) and cloud-based solutions, can provide some level of secure and compliant storage, but lack the following requirements:

Data Security: Conventional cloud-based and on-premise data management solutions carry significant security vulnerabilities that hackers can exploit. In particular, managing access to core data assets using role-based access controls carries significant risk of breach as these roles can be mirrored or spoofed. Once a breach occurs, the hacker gains access to all data that is accessible to that role, which can be extensive in the case of administrative roles.

Data Ownership: Both in the United States and globally, new data privacy laws are defining legal ownership of data, and requiring that data owners have functional, rather than theoretical, control over their data assets. Given that health data is comprised of a complex mixture of patient clinical data, provider operational data, consumer lifestyle and Internet-of-things (IoT) data, clinical research data, and public (e.g., environmental and public records) data, establishing ownership of health data can be complex, requiring more robust data management tools than traditional systems can accommodate. In particular, a data management system would ideally include the ability to enforce ownership at highly granular levels (i.e., down to the individual data point level) and based on individual owners as opposed to types of owners (or roles). The system would also ideally support complex ownership structures (e.g., multiple owners of a single data asset, data custodian and escrow models), and be powerful enough to manage all of these requirements at scale (e.g., with terabytes of data).

Data Sharing: To ensure the secure exchange of data, traditional data management systems typically require direct integrations, secure file transfer systems, or similar methods for physically transferring data from one repository to another. These so-called "direct transfer systems" present several challenges. First, it can be difficult and expensive to implement such systems at scale, where thousands of end-points, or more, need to exchange data. Second, if the data owner only has direct control over the "transfer from" repository and has no control of the "transfer to" repository, the act of transferring data will effectively cause the data owner to lose functional control over their data, including visibility into any changes to or downstream sharing of that data. This is a significant problem for data exchange systems needing to maintain compliance with data privacy laws.

To address the above challenges and limitations, the present embodiments include methods for consent-based data sharing within a blockchain using smart contracts. Referred to herein as "consent contracts", these smart contracts enable data ownership at the level of individual and multiple owners. Consent contracts may be advantageously used, for example, by clinical researchers for collaborative research, federated learning across communities of anonymized contributors, and specific data exchange between stakeholders in a clinical study. The present embodiments also include a secure adaptive data storage platform with which the blockchain and consent contracts can be implemented. This secure adaptive data storage platform enables health-related organizations (e.g., providers, payers, technology service providers, and health information exchanges) to provide efficient and patient-centric care by making health data available to analytical tools and services, and by accessing new data sources that drive additional insight and value. With this platform, organizations, public agencies, researchers, and individuals can actively connect with each other throughout the world to form partnerships and relationships based on the secure and compliant exchange of data.

An owner consent contract is one type of smart contract in which a data owner grants, to other entities or a group of entities (e.g., individuals, companies, institutions, providers, etc.) having access to the blockchain, read-only access to assets (i.e., data) that are owned by the owner and stored in the blockchain. The consent contract answers the questions: "Which entity, if any, should get access to my data?" and "Which elements of that data should they see?" During a query performed on the blockchain, explicit rights determined by an owner consent contract are enforced in view of implicit rights (i.e., those inherent to the owner).

A global consent contract is similar to an owner consent contract except that it applies more widely (i.e., to multiple data owners). Advantageously, global consent contracts may be used to globally (i.e., throughout the entire blockchain) enforce certain privacy rules, such as those required by institutional, legislative, and/or governmental bodies. The global access rules specified in a global consent contract may either supersede, or be superseded by, the access rules specified in owner consent contracts. Accordingly, the combination of owner and global consent contracts creates two "layers" of access to any given block of data. This idea of layered consent can be extended to three or more layers.

Each owner consent contract and global consent contract is stored in the blockchain as an asset in a corresponding consent block, similar to how each data asset (e.g., medical data, personal health information (PHI), personal identifying information (PII), etc.) in stored in the blockchain in a data block. Each consent block, once added to the blockchain, becomes part of the immutable record of data stored in the blockchain, and thus leaves an auditable trail of which entities currently have and previously had access to which data, when, and under what conditions.

In embodiments, a blockchain access method includes adding to a blockchain a consent block storing a global consent contract containing one or more global access rules that determine access, for an entity other than an owner of the global consent contract, to a portion of an asset that is stored in another block of the blockchain, the asset being having an owner that is different from the entity. The consent block also stores a hash value determined from at least the global consent contract and a previous hash value of a block, of the blockchain, immediately preceding the consent block. The global consent contract and a position of the consent block in the blockchain are verifiable from the hash value.

In other embodiments, a blockchain access method includes searching, in response to a request from an entity, a blockchain formed from a series of blocks, each of the blocks storing an asset and having an owner. The searching identifies (i) at least one owner consent contract containing one or more owner-specified access rules that determine access for the entity to a portion of an asset that is stored in another block of the blockchain and owned by the owner of the at least one owner consent contract. The searching also identifies (ii) at least one global consent contract containing one or more global access rules that determine access for the entity to the portion of the asset. The blockchain access method also includes querying the blockchain, based on the one or more owner-specified access rules and the one or more global access rules, to identify a plurality of allowed blocks, of the blockchain, containing assets that the entity may access. Each allowed block has an owner different from the entity. The blockchain access method also includes retrieving, for each of the allowed blocks, a portion of the asset stored therein. The portion of the asset may consist of the entire asset.

BRIEF DESCRIPTION OF THE FIGURES

FIG. 4 shows a one-to-one consent contract in which a single owner of a one-to-one consent contract grants access to a single entity, in an embodiment.

FIG. 5 is a one-to-many consent contract that is similar to the one-to-one consent contract of FIG. 4 except that it grants access to more than one entity, in an embodiment.

FIG. 6 shows a one-to-type consent contract that is similar to the one-to-one consent contract of FIG. 4 except that access is granted to an entity type as opposed to a specific identity having an explicit address, in an embodiment.

DETAILED DESCRIPTION OF THE EMBODIMENTS

Figure 1:
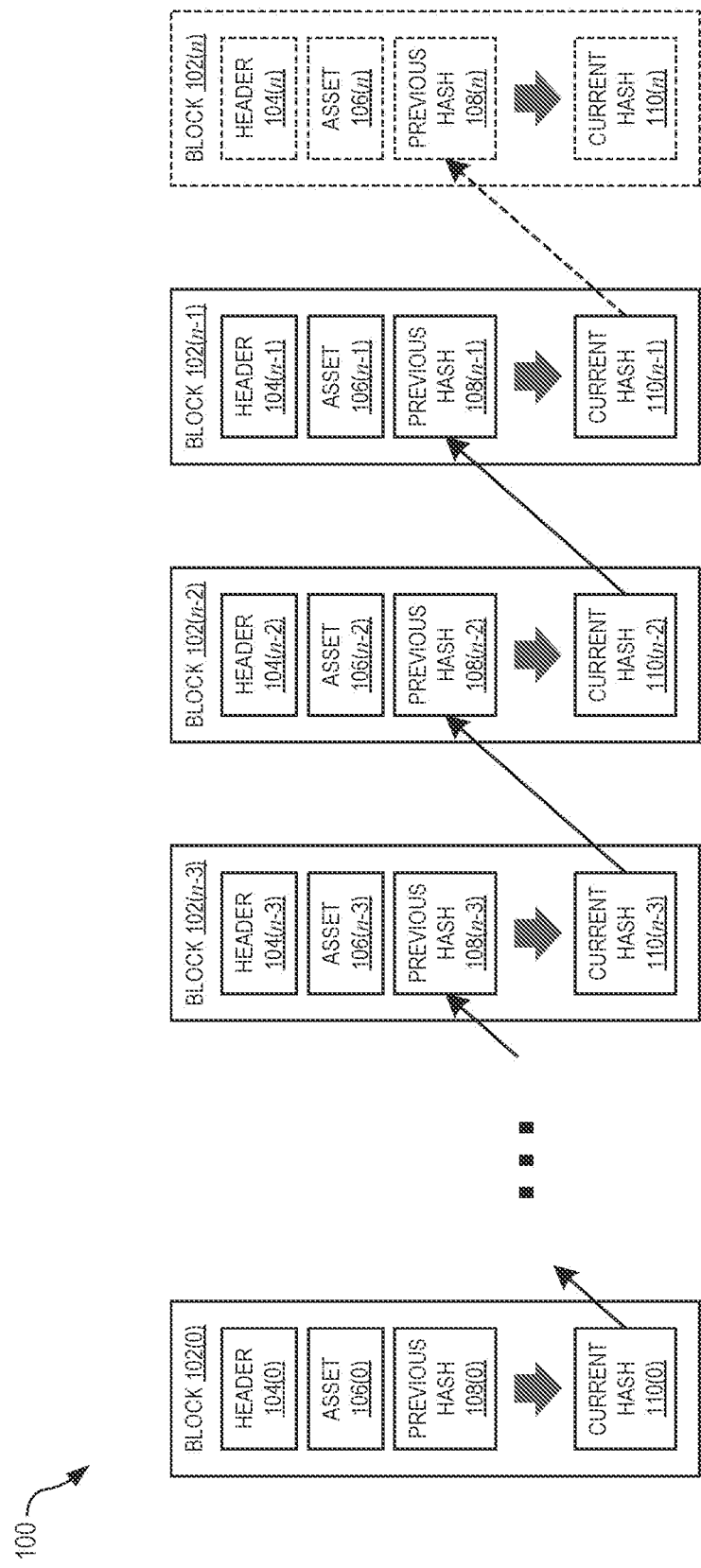
FIG. 1 shows a series of n blocks being cryptographically linked to form a blockchain.

FIG. 1 shows a series of n blocks 102 being cryptographically linked to form a blockchain 100. Each block 102 stores header information 104, an asset 106, a previous hash value 108, and a current hash value 110. The blocks 102, when cryptographically linked, form an ordered sequence in which each block 102 is uniquely indexed. For clarity, each block 102 is labeled with an index in parentheses that identifies a position of that block 102 in the blockchain 100. For example, the $i^{th}$ block 102 is labeled block 102($i$), and stores similarly indexed header information 104($i$), asset 106($i$), previous hash value 108($i$), and current hash value 110($i$). The blockchain 100 begins with an origin block 102(0). The number of blocks n in the blockchain 100 may be millions, or more. For clarity in FIG. 1, only the origin block 102(0) and the four most-recent blocks 102($n$-3), 102($n$-2), 102($n$-1), and 102($n$) are shown.

Identical copies of the blockchain 100 may be stored on multiple computing nodes that cooperate as a peer-to-peer distributed computing network to implement the blockchain 100 as one type of distributed ledger. In this case, the nodes cooperate to add new blocks 102 to the blockchain 100 in a decentralized manner (i.e., without a central authority or trusted third party). Specifically, a consensus protocol may be implemented to validate data to be appended to the blockchain 100. Once validated by a node, the node broadcasts the validated data to all other nodes, which then update their local copy of the blockchain 100 by appending the validated data to the blockchain 100 as a new block 102. Validation may be implemented via proof-of-work, proof-of-stake, modified proof-of-stake, or another type of consensus protocol. Once a block 102 is added to the blockchain 100, it can only be modified via collusion of a majority of the nodes (i.e., a 51% attack). Since such collusion is considered highly unlikely, the blockchain 100 is secure by design.

The blockchain 100 is therefore similar to many blockchain-based cryptocurrencies (e.g., Bitcoin, Ethereum, etc.) that process and store data related to financial transactions. However, the blockchain 100 (specifically, the asset 106 stored in each block 102) may store any type of data without departing from the scope hereof. Advantageously, data stored in the blockchain 100 is essentially immutable, and thus can be readily verified during an audit. In the following discussion, the asset 106 includes personal health information (PHI) and personal identifying information (PII) that are encrypted. PHI includes any information about health status, provision of health care, and/or payment of health care, and can be linked to a specific individual. Examples of PHI include medical records and laboratory results. PHI may also include PII. Examples of PII include name, social security number, and date-of-birth. However, the asset 106 may store any other type of data without departing from the scope hereof. The asset 106 may alternatively be unencrypted, or a combination of encrypted and unencrypted.

Although not shown in FIG. 1, the blockchain 100 may also have a unique name or identifier such that the blockchain 100 can be identified among similar blockchains that are also stored and implemented on the same computing platform. Thus, the blockchain 100 need not be the only blockchain on the computing platform.

FIG. 1 also shows a new block 102($n$) being added to the blockchain 100 so that it is cryptographically linked to a previous block 102($n$-1). The current hash value 110($n$-1) of the previous block 102($n$-1) is copied and stored as the previous hash value 108($n$) of the new block 102($n$). Thus, the current hash value 110($n$-1) equals the previous hash value 108($n$). The current hash value 110($n$) may then be determined by hashing the header information 104($n$), asset 106($n$) and previous hash value 108($n$) stored in the new block 102($n$). For example, the header information 104($n$), asset 106($n$), and previous hash value 108($n$) may be concatenated into a single string that is inputted to a cryptographic hash function whose output is stored as the current hash value 110($n$). Alternatively, the header information 104($n$), asset 106($n$), and previous hash value 108($n$) may be pair-wise hashed into a Merkle tree whose root node is stored as the current hash value 110($n$). Other ways of using the cryptographic hash function to generate the current hash value 110($n$) may be used without departing from the scope hereof.

Advantageously, the current hash values 110 provide an efficient way to identify any change to any data stored in any block 102, thereby ensuring both the integrity of the data stored in the blockchain 100 and the order of the blocks 102 in the blockchain 100. To appreciate how the current hash values 110 enforce data integrity and block order, consider a change made to one or more of the header information 104($i$), the asset 106($i$), and the previous hash value 108($i$) of the block 102($i$) (where i is any integer between 1 and n). The change may be detected by rehashing the block 102($i$) and comparing the result with the current hash value 110($i$) stored in the block 102($i$). Alternatively or additionally, the rehash may be compared to the previous hash value 108($i$+1) stored in the subsequent block 102($i$+1). Due to the change, the rehash value will not equal the current hash value 110($i$) and the previous hash value 108($i$+1). These unequal hash values can be used to identify an attempt to alter the block 102($i$). Assuming no entity controls a majority of the voting power (i.e., no collusion), such attempts at modifying any data anywhere in the blockchain 100 will be rejected due to the consensus protocols described above.

Accordingly, the blockchain 100 may be verified via two steps. First, for each block 102($i$), a rehash of the header information 104($i$), asset 106($i$), and previous hash value 108($i$) may be compared to the current hash value 110($i$) to ensure that the rehash equals the current hash value 110($i$). This first step authenticates the data stored within each block 102. Second, for each block 102($i$), the previous hash value 108($i$) may be compared to the current hash value 110($i$-1) of the previous block 102($i$-1) to ensure that these values are equal. This second step authenticates the order of the blocks 102. Verification of the blockchain 100 may proceed "backwards", i.e., sequentially verifying each block 102 starting from the most-recent block 102($n$) and ending at the origin block 102(0). Alternatively, verification may proceed "forwards", i.e., sequentially verifying each block 102 starting from the origin block 102(0) and ending with the most-recent block 102($n$). Validation may occur periodically (e.g., once every hour or day), in response to one or more new blocks 102 being added to the blockchain 100, or according to a different schedule, different triggering events, or a combination thereof. For the origin block 102(0), the previous hash value 108(0) may be set to an arbitrarily-chosen value.

In FIG. 1, each block 102($i$) is shown storing its current hash value 110($i$). However, it is not necessary for each block 102($i$) to store its current hash value 110($i$) since it can always be generated by hashing the other data stored in the block 102($i$). Nevertheless, storing the current hash value 110($i$) with each block 102($i$) can greatly speed up retrieval of the blocks 102, and thus access to the asset 106, by using the current hash values 110 as search keys in a database index. For example, each current hash value 110($i$) may be represented as a node in a binary search tree (e.g., a B-tree, a self-balancing binary search tree, a fractal tree index, etc.). Each node may also store the corresponding index i. When the new block 102($n$) is added to the blockchain 100, its owner (see owner id 208 in FIG. 2) may be given the resulting current hash value 110(n) as a "receipt". When the owner wishes to subsequently retrieve the corresponding asset 106(n) from the blockchain 100, the owner may submit a request containing the receipt. The binary tree may be searched to quickly (i.e., faster-than-linear in the number n of nodes) find the index n. The block 102(n) may then be directly accessed (e.g., from secondary storage) without having to sequentially search the blocks 102. As an additional check, the receipt may be compared to the current hash value 110(n) of the retrieved block 102(n) to ensure the values match.

Figure 2:
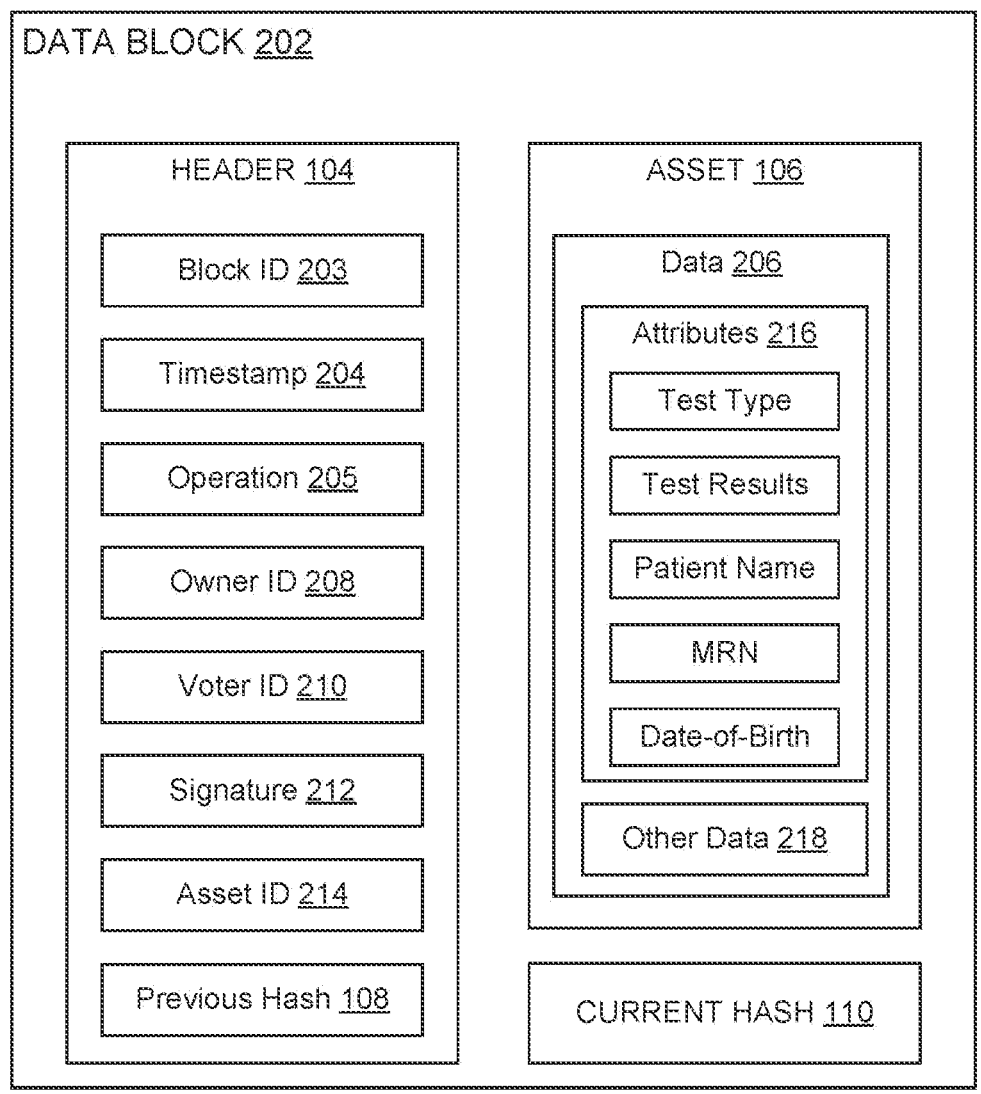
FIG. 2 shows a data block storing data as an asset, in an embodiment.

FIG. 2 shows a data block 202 storing data 206 as the asset 106. The data block 202 is one type of block 102, and thus any of the blocks 102 in FIG. 1 may be a data block 202. In FIG. 2, the asset 106 stores data 206 as attributes 216, i.e., named data variables with stored values that can be retrieved by name. In the example of FIG. 2, the attributes 216 are listed by name: "test type", "test results", "patient name", medical record number "MRN", patient "date-of-birth". While these attributes 216 are examples of PHI and PII, the attributes 216 may be any type of data, or combination of data types, without departing from the scope hereof. The asset 106 may store additional or alternative attributes 216 than shown. The attributes 216 represent one way in which data 206 may be organized and stored in the asset 106; the asset 106 may additionally or alternatively store other data 218 without departing from the scope hereof.

For clarity in FIG. 2, the header information 104 is shown storing the previous hash value 108. Thus, when the header information 104 is hashed, the previous hash value 108 is included. The header information 104 may also include a block identifier (ID) 203 that uniquely labels the data block 202. For example, the block ID 203 may be an integer-valued index identifying the position of the data block 202 in the blockchain 100. The header information 104 may also include a timestamp 204 identifying the date and/or time when the data block 202 was created (i.e., added to the blockchain 100). The header information 104 may also include an operation 205 identifying how the data block 202 is used by the blockchain 100. For example, the operation 205 may be a text string (e.g., "create") indicating that the block 102 is a data block 202 storing data 206. Other examples of the operation 205 are described in more detail below.

The header information 104 may also include an owner ID 208 that stores information identifying one or more entities (e.g., individuals, jurisdictions, companies, etc.) that own the asset 106, and thus control access to the asset 106. The owner ID 208 may be, for example, one or more publicly available address strings that uniquely identify the corresponding one or more entities that own the data block 202. The header information 104 may also include a voter ID 210 that stores information identifying the one node of the distributed computing network that first verified the data block 202. The voter ID 210 may be a publicly available address string that uniquely identifies the one node.

The header information 104 may also include a signature 212 that is formed when the owner of the data block 202 cryptographically signs the current hash 110 with a private key (e.g., from a RSA key pair). Advantageously, the signature 212 allows an entity to verify the integrity of the asset 106 (i.e., that the asset 106 has not been altered since it was added to the blockchain 100) and the owner of the asset 106. Specifically, the entity can use the owner's public key to "unlock" the signature 212 and compare the result to a rehash of the data block 202 (i.e., a rehash of the header information 104 and asset 106). If these values agree, both the integrity of the asset 106 and the owner are verified. However, if these values do not agree, then the source of the public key may not be the true owner of the block, or the asset 106 may have been altered subsequent to its addition to the blockchain 100.

The header information 104 may also include an asset ID 214 that stores information identifying the asset 106. Since the asset 106 is essentially immutable, any change to the asset 106 is implemented by adding the changed asset 106 to the blockchain 100 in a new data block 202. For example, consider a first data block 202(i) with a first asset 106(i). The owner then changes the first asset 106(i) into a second asset 106(j) that is stored in a subsequent second data block 202(j). Both the first and second data blocks store the same asset ID 214, indicating that the second data block 202(j) replaces the first data block 202(i). Thus, the second asset 106(j) is essentially a newer version of the first asset 106(i). When retrieving the asset 106 from the blockchain 100, only the latest version (i.e., most-recent) of the asset 106 is returned.

The blockchain 100 may be implemented as a database whose records correspond to the blocks 102. Since the asset 106 may be stored in different formats, the database may be a document-oriented database (e.g., MongoDB) or another type of NoSQL database. Alternatively, the database may be a relational database in which the asset 106 is represented in table form. In any case, implementing the blockchain 100 in a database advantageously allows the blocks 102 to be searched and retrieved with faster-than-linear time scaling.

When the blockchain 100 is implemented as a database, the blocks 102 may be advantageously accessed using database query techniques and commands known in the art. Any of the data stored in the block header 104 may be used, as part of a query, to develop logical statements that define a set of one or more selection criteria. A database management system (DBMS) executes the query to identify which of the blocks 102 meet the selection criteria. Specifically, the DBMS may access each block 102(i) sequentially (e.g., starting from the origin block 102(0) and ending at the most-recent block 102(n)) to determine whether the block 102(i) meets the selection criteria. Blocks 102 identified as meeting the selection criteria are grouped into a result set. Each block 102 in the result set may then be accessed to retrieve a copy of its corresponding asset 106.

Figure 3:
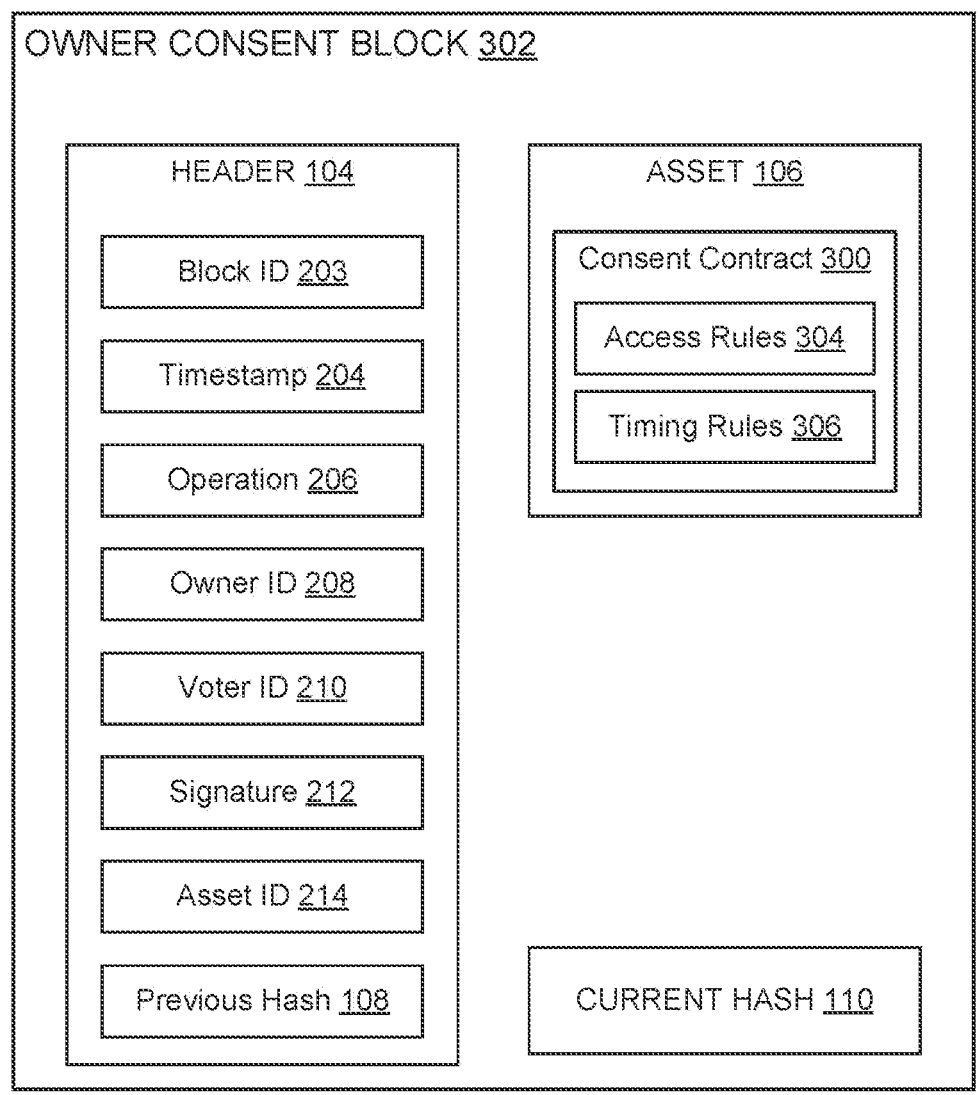
FIG. 3 shows an owner consent block that is similar to the data block of FIG. 2 except that it stores an owner consent contract as its asset instead of data, in an embodiment.

FIG. 3 shows an owner consent block 302 that is similar to the data block 202 of FIG. 2 except that it stores an owner consent contract 300 as its asset 106 instead of data 206. The owner consent block 302 is one type of block 102, and thus any of the blocks 102 in FIG. 1 may be an owner consent block 302. The owner consent contract 300 is a type of smart contract that allows its owner (as identified by the owner ID 208) to grant read-only access to the data 206 stored in data blocks 202 that are also owned by the same owner. The access is granted to one or more entities whose owner IDs are different from that of the owner.

The owner consent contract 300 may also include timing rules 306 that determine when the owner consent 300 is active. The timing rule 306 may include an expiration date such that access granted by the owner consent contract 300 ceases after the expiration date. The timing rules may also include an expiration time such that the owner consent contract 300 ceases after the expiration time on the expiration date. The timing rules 306 may include a future start date (and optional future start time) after which the owner consent contract 300 takes effect. When the timing rules 306 include both start and expiration dates, the owner consent contract 300 will only be active during the time window bounded by the start and expiration dates (assuming the expiration date comes after the start date).

The owner consent contract 300 stores one or more owner-specified access rules 304 in the form of commands (i.e., machine-readable instructions) that add to and/or modify the selection criteria of a query that is executed on the blockchain 100. In one example of their use, the blocks 102 of the blockchain 100 are sequentially accessed, in response to a query, to identify all relevant owner consent contracts 300 stored in the blockchain 100. In this first pass through the blocks 102, only the owner consent blocks 302 are accessed (i.e., the data blocks 202 are ignored). The access rules 304 from these owner consent contracts 300 are combined with the selection criteria defined by the query to create an augmented set of selection criteria. For example, the owner-specified access rules may be joined (e.g., conjunctively or disjunctively) with the query selection criteria to form the augmented selection criteria. The blocks 102 are then accessed a second time to create a result set of data blocks 202 that meet the augmented selection criteria. The asset 106 of each data block 202 in the result set may then be accessed and retrieved.

FIGS. 4-6 show examples of how the owner consent contract 300 grants access to data 206 in data blocks 202. FIG. 4 shows a one-to-one consent contract 400 in which a single owner of the one-to-one consent contract 400 grants access to a single entity. The one-to-one consent contract 400 is one example of the owner consent contract 300. The single owner is identified by the one owner ID 208 of the corresponding owner consent block 302. In the first line of the one-to-one consent contract 400, an address following the keyword consents is a public identifier identifying the entity receiving the access. In the second line of the one-to-one consent contract 400, the text "for chain_name" indicates that the one-to-one consent contract 400 only applies to the blockchain with the name or identifier chain_name.

In the third line of the one-to-one consent contract 400, the keyword when is followed by a logical statement that must be satisfied for access to be granted. In the example of FIG. 4, the logical statement is true when the asset ID 214 of a data block 202 (i.e., asset.identifier) equals the fixed value 15131. Accordingly, the one-to-one consent contract 400 only grants access to the data 206 in a data block 202 having (1) the fixed value as its asset ID 214, and (2) the same owner (i.e., owner ID 208) as the one-to-one consent contract 400. The logical statement following the keyword when may include several fixed values for the asset ID (e.g., separated by commas or spaces). In this case, the logical statement is true when a data block 202 stores any one of these fixed values for its asset ID 214. Alternatively, the logical statement may include a wildcard symbol * to indicate that access is granted to all of the owner's data 206, regardless of the asset ID 214.

Alternatively, the logical statement may include one or more types of assets. For example, the one-to-one consent contract 400 may include a statement when asset.test_type=attribute_value. In this case, when the data 202 includes an attribute 216 named test_type, the value stored therein is checked to see if it equals attribute_value. If so, access to the data 206 in the data block 202 is granted. If not, or if there is no attribute 216 with the name test_type, then access to the data block 202 is not granted. Many co-owned data blocks 202 may store the value attribute_value in the attribute named test_type, but with different asset IDs 214. In this case, the different asset IDs may indicate that the patient had the same test performed several times. The one-to-one consent contract 400 may grant access to all of these data blocks 102 without regard to the asset ID 214. Alternatively, the logical statement may combine requirements for asset.test_type and asset.identifier to limit access to only some (e.g., one) of the data blocks 102 in which the attribute named test_type stores the value attribute_value.

In the fourth line of the one-to-one consent contract 400, the keyword until is followed by a date indicating that the one-to-one consent contract 400 expires as of the specified date and time. The specified date and time is one example of the timing rules 306 shown in FIG. 3. In the fifth line of the one-to-one consent contract 400, the keyword "only" is followed by a list of attribute names. Access is only granted to an attribute 216 whose name matches one of those listed (i.e., attr3, attr4, and attr5 in the example of FIG. 4).

FIG. 5 shows a one-to-many consent contract 500 that is similar to the one-to-one consent contract 400 of FIG. 4 except that it grants access to more than one entity. In this case, two entities are identified by two addresses that appear after the keyword consents. However, the one-to-many consent contract 500 may be expanded to grant access to more than two entities by listing additional addresses after the keyword consents.

FIG. 6 shows a one-to-type consent contract 600 that is similar to the one-to-one consent contract 400 of FIG. 4 except that access is granted to an entity type as opposed to a specific identity having an explicit address. In FIG. 6, the entity type is 'researcher'. An entity accessing the blockchain 100 may be labeled according to one or more predefined entity types. For example, when an entity is labeled 'researcher', the one-to-type consent contract 600 may grant access to the entity. If the entity is not labeled 'researcher' (e.g., 'clinic', 'practitioner', 'insurer', etc.), the one-to-type consent contract 600 will not grant access to the entity. An entity may have more than one entity type. Similar to the one-to-many consent contract 500 of FIG. 5, multiple entity types may be granted access using one one-to-type consent contract 600, e.g., by listing the multiple entity types after the keyword. In addition, one or more specific addresses may be listed with the multiple entity types, wherein the one-to-type consent contact 600 grants access to specific entities in addition to the one or more entity types.

An owner can add to the blockchain 100 several owner consent contracts 300 stored in several corresponding owner consent blocks 302, thereby giving the owner the flexibility to determine who can access the owner's data blocks 202, what parts of the assets 106 they can access, and under what conditions. Each owner consent block 302 includes an asset ID 214 with which the owner can update the owner consent contract 300. For example, the owner of the owner consent block 302 may add to the blockchain 100 a new owner consent block 302 with the same asset ID 214 and an owner consent contract 300 with updated access rules 304 (and/or updated timing rules 306). In this case, the updated access rules 304 supersede (i.e., take precedence over) the original access rules 304, thereby allowing the owner to revise the original access rules 304 at any time after they have been added to the blockchain 100. When the blocks 102 of the blockchain 100 are sequentially accessed to identify all relevant owner consent contracts 300, only the most recent owner consent contract 300 with a particular asset ID 214 is used, i.e., all previous owner consent contracts 300 with the same asset ID 214 are ignored, as their corresponding owner-specified access rules 304 have been superseded.

An owner may create several owner consent contracts 300 that work together to determine access granted to one or more entities. Thus, the owner is not limited to issuing only one owner consent contract 300 for a single entity. Rather, the owner can create multiple owner consent contracts 300, each stored in a corresponding owner consent block 302 with a different asset ID 214 and containing access rules 304 for the same entity. In this case, due to the different asset IDs 214, access granted to the entity is determined by all of the access rules 304 stored in all of the consent contracts 300 identifying the entity. As a result, no access rules 304 supersede, or are superseded by, other access rules 304. In this case, the access rules 304 from the several owner consent contracts 300 may be combined (e.g., conjunctively or disjunctively) to determine the access granted to the entity.

Figures 7, 8:
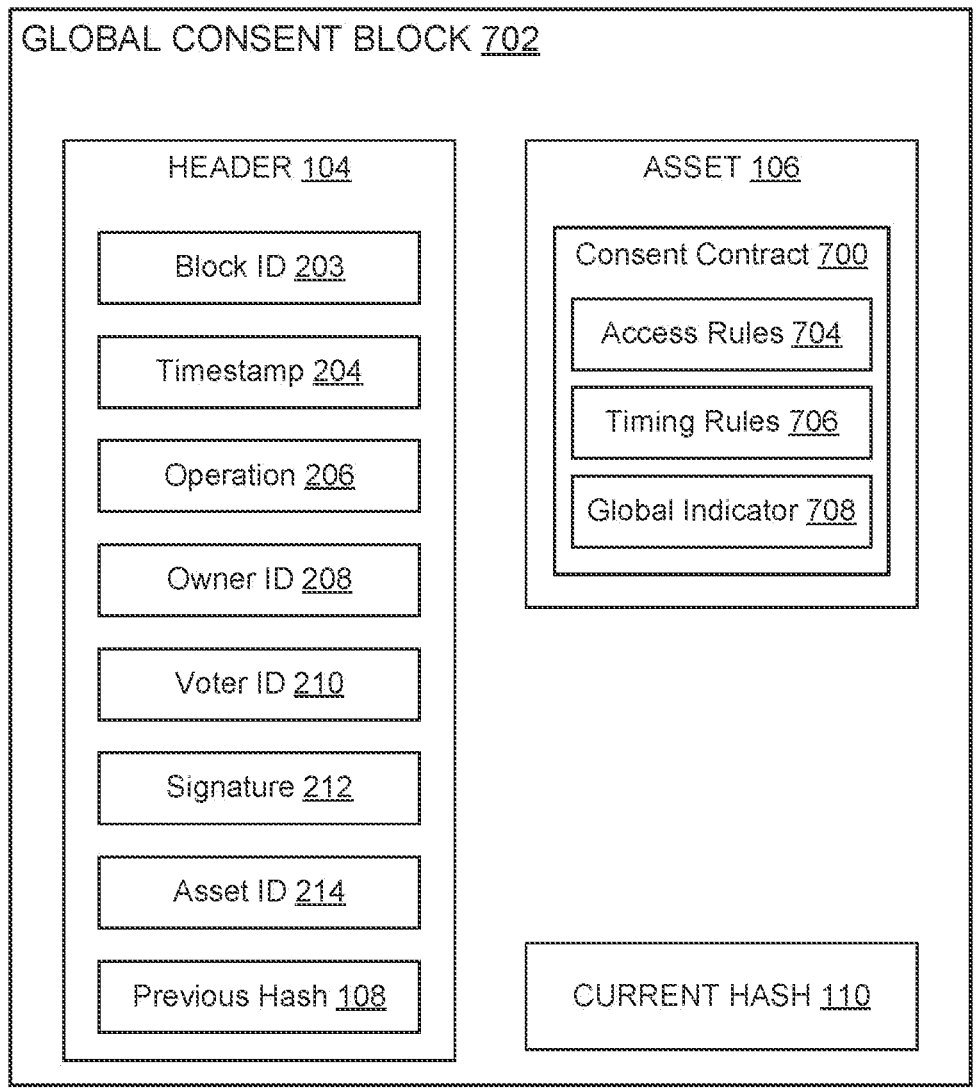
FIG. 7 shows a global consent contract that is similar to the owner consent block of FIG. 3 except that it stores a global consent contract with global consent rules takes supersede owner-specified access rules, in an embodiment.
FIG. 8 shows two global consent contracts that are examples of the global consent contract of FIG. 7, in embodiments.
Figure 9:
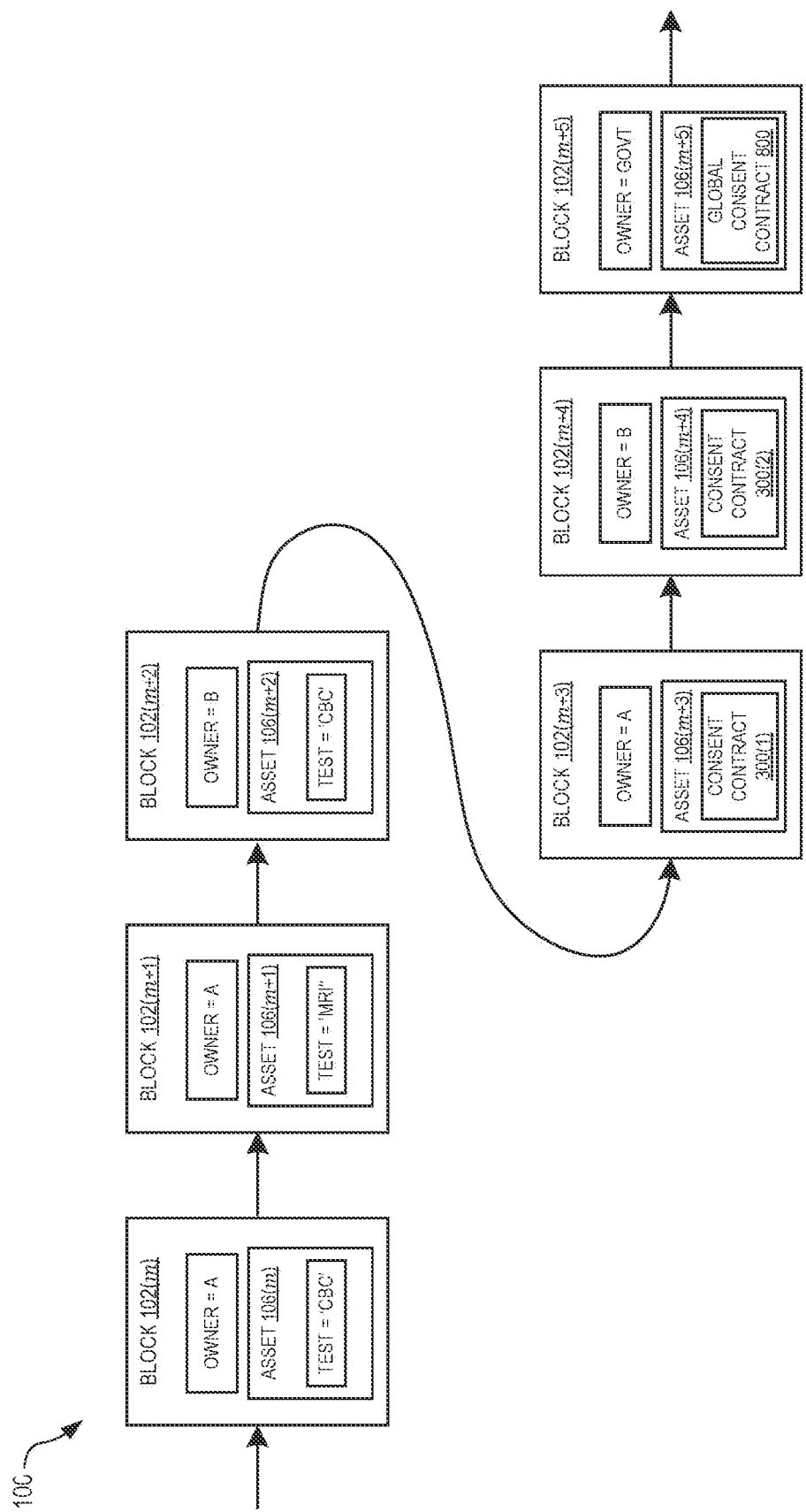
FIG. 9 illustrates how the global consent contracts of FIG. 8 implement additional "layers" of access to the blockchain of FIG. 1, in an embodiment.

FIG. 7 shows a global consent block 702 that is similar to the owner consent block 302 of FIG. 3 except that it stores a global consent contract 700 with global access rules 704 that supersede owner-specified access rules 304. FIG. 8 shows global consent contracts 800 and 810 that are examples of the global consent contract 700. FIG. 9 illustrates how the global consent contracts 800 and 810 implement additional "layers" of access to the blockchain 100. FIGS. 7-9 are best viewed together with the following description.

The global consent contract 700 is similar to the owner consent contract 300 in that it stores access rules as its asset 106, and stores timing rules 706 similar to timing rules 306. Thus, the global consent contract 700 may be stored in the blockchain 100 and used similarly to an owner consent contract 300. However, the global consent contract 700 specifies global access rules 704 that supersede, or take precedence over, owner-specified access rules 304. Thus, the global consent contract 700 introduces an additional layer of access to the blockchain 100. For example, where an owner consent contract 300 grants access to an entity, the global consent contract 700 may block that access. Alternatively, where an owner consent contract 300 does not grant access to an entity, the global consent contract 700 may grant access. Global consent contracts 700 may be utilized in situations where data access must be managed at various institutional, legislative, and/or governmental levels. For example, government regulations (e.g., the General Data Protection Regulation (GDPR) in the European Union) may impose certain time limits within which data must be used, or within which data use is restricted.

In the global consent contract 800 of FIG. 8, the keyword global is included after the keyword consents to indicate that the consent contract is a global consent contract 700, and not an owner consent contract 300. The keyword suppress after the keyword global indicates that the global consent contract 800 restricts access to data that may be otherwise granted by an owner consent contract 300. The wildcard symbol * after the keyword suppress indicates that the global consent contract 800 applies to every owner. The keyword when is used similarly as in the owner-consent contract 300 to generate one or more of the global access rules 704. In the example of FIG. 8, the third line of the global consent contract 800 indicates that access to the asset 106 is blocked when the asset 106 has an attribute named 'test' storing the value 'CBC' (i.e., when the asset 106 stores results for a complete blood count, or CBC test).

FIG. 9 shows a portion of the blockchain 100 containing six blocks 102(m) through 102(m+5). For clarity in FIG. 9, each block 102 only shows an owner and a portion of the corresponding asset 106 (i.e., an attribute named "Test"). In a first block 102(m), a first owner A stores CBC test results in the corresponding asset 106(m). In a second block 102(m+1), the first owner A stores MRI test results (e.g., one or more MRI images) in the corresponding asset 106(m+1). In a third block 102(m+2), a second owner B stores CBC test results in the corresponding asset 106(m+2). In a fourth block 102(m+3), the first owner A has created an owner consent contract 300(1) granting access to any asset 106 owned by A to a specified entity. In a fifth block 102(m+4), the second owner B has an owner consent contract 300(2) granting access to any asset 106 owned by B to a type of entity. In a sixth block 102(m+5), a government entity has created the global consent contract 800 (see FIG. 8) to restrict access to any CBC test result stored in the blockchain 100.

When the blockchain 100 is queried by an entity, the owner-specified access rules 304 obtained from the owner consent contracts 300(1) and 300(2) are combined with the global access rules 704 of the global consent contract 800 to create a composite set of selection criteria. The blocks 102 are then sequentially accessed, using the composite set of selection criteria to create a result set RS that can be generally expressed as $$RS = O_t + \left[ \bigcup_{i=1}^{N} CC_i \subseteq X_i - \bigcup_{j=1}^{M} = GCC_j \right] \quad (1)$$

where i is an index over N owner consent contracts 300 found in the blockchain 100, $X_i$ is set of all blocks 102 owned by the owner of the ith owner consent contract 300(i), $CC_i$ is the subset of $X_i$ to which access has been granted to the querying entity, j is an index over M global consent contracts 700 found in the blockchain 100, and $GCC_j$ represents blocks 102 the querying entity is not allowed to access due to the jth global consent contract 700(j). As indicated by the minus sign in Eqn. 1, the effect of each global consent contract 700 is to remove blocks from the result set RS that would otherwise be included based on the owner consent contracts 300. Eqn. 1 also shows how multiple owner consent contracts 300 and/or multiple global consent contracts 700 can be used to determine the result set RS. The second and third terms on the right-hand side of Eqn. 1 represent blocks 102 that are not owned by the querying entity, but to which the querying entity has been granted access. The result set RS may also include $O_t$, which is the set of all blocks 102 owned by the querying entity. An entity can always access the blocks 102 that it owns.

Applying Eqn. 1 to the example of FIG. 9, the global consent contract 800 prevents the entity specified in the owner consent contract 300(1) from accessing A's CBC test results in the block 102(m), even though A granted such access. In fact, the global consent contract 800 prevents any entity from accessing A's CBC test results. Similarly, the global consent contract 800 prevents any entity specified in the owner consent contract 300(2) from accessing B's CBC test results in the block 102(m+2), even though B granted such access. Furthermore, B did not grant any entity access to the MRI test results stored in the block 102(m+1), and therefore no entity can access these data results, regardless of the global consent contract 800.

In the preceding discussion, the global consent contract 700 stored global access rules 704 that supersede owner-specified access rules 304. However, the global consent contract 700 may be implemented such that owner-specified access rules 304 supersede the global access rules 704. For example, the global access rules may specify a maximum level of access (e.g., as allowed by law). An owner consent contract 300 may then impose stricter owner-specified access rules 304 to further block access above what is required by law.

In other embodiments, a blockchain access method includes adding to a blockchain a consent block storing a global consent contract containing one or more global access rules that determine access, for an entity other than an owner of the global consent contract, to a portion of an asset that is stored in another block of the blockchain. The asset has an owner that is different from the entity. The consent block also stores a hash value determined from at least the global consent contract and a previous hash value of a block, of the blockchain, immediately preceding the consent block. The global consent contract and a position of the consent block in the blockchain are verifiable from the hash value. The portion of the asset may consist of either the entire asset or a subset thereof. The one or more global access rules may block access to the entity from viewing the portion of the asset.

In one embodiment, the global access rules supersede access rules from owner consent contracts stored in other blocks of the blockchain. In another embodiment, the global access rules are superseded by the access rules from owner consent contracts stored in other blocks of the blockchain. In embodiments, the one or more global access rules determine access to the portion of the asset based on a specified asset type of the asset. In embodiments, the one or more global access rules include one or more attributes that identify the portion of the asset to which the access is determined. In embodiments, the one or more global access rules include a type of entity that determines a plurality of entities to which said global access rules apply.

In one example of this blockchain access method, the global consent block 702 of FIG. 7 stores the global consent contract 700 that determines global access rules 704. The consent block may additionally store a timestamp indicating when it was added to the blockchain, and a public identifier identifying the owner of the owner consent contract (e.g., see the timestamp 204 and owner ID 208 stored in the global consent block 702 of FIG. 7). The consent block may also store an asset identifier that identifies the global consent contract stored therein (e.g., see the asset ID 214 stored in the global consent block 702).

In other embodiments, a blockchain access method includes searching, in response to a request from an entity, a blockchain formed from a series of blocks, each of the blocks storing an asset and having an owner, to identify: (i) at least one owner consent contract containing one or more owner-specified access rules that determine access for the entity to a portion of an asset that is stored in another block of the blockchain and owned by the owner of the at least one owner consent contract; and (ii) at least one global consent contract containing one or more global access rules that determine access for the entity to the portion of the asset. The blockchain access method also includes querying the blockchain, based on the one or more owner-specified access rules and the one or more global access rules, to obtain a plurality of allowed blocks, of the blockchain, containing assets that the entity may access. The blockchain access method also includes retrieving, for each of the allowed blocks, a portion of the asset stored therein. The portion of the asset may consist of either the entire asset or a subset thereof.

The one or more owner-specified access rules may include a public identifier that identifies the entity. The one or more global access rules may supersede the one or more owner-specified access rules. Alternatively, the one or more global access rules may be superseded the one or more owner-specified access rules. Alternatively, some of the global access rules may supersede some of the owner-specified access rules, while others of the global access rules are superseded by others of the owner-specified access rules. The at least one owner consent contract may include an updated owner consent contract containing one or more updated owner-specified access rules that replace the one or more owner-specified access rules. In this case, querying the blockchain is based on the one or more updated owner-specified access rules instead of the one or more owner-specified access rules. In some embodiments, the blockchain access method further includes outputting the portion of the asset after retrieving.

Figure 10:
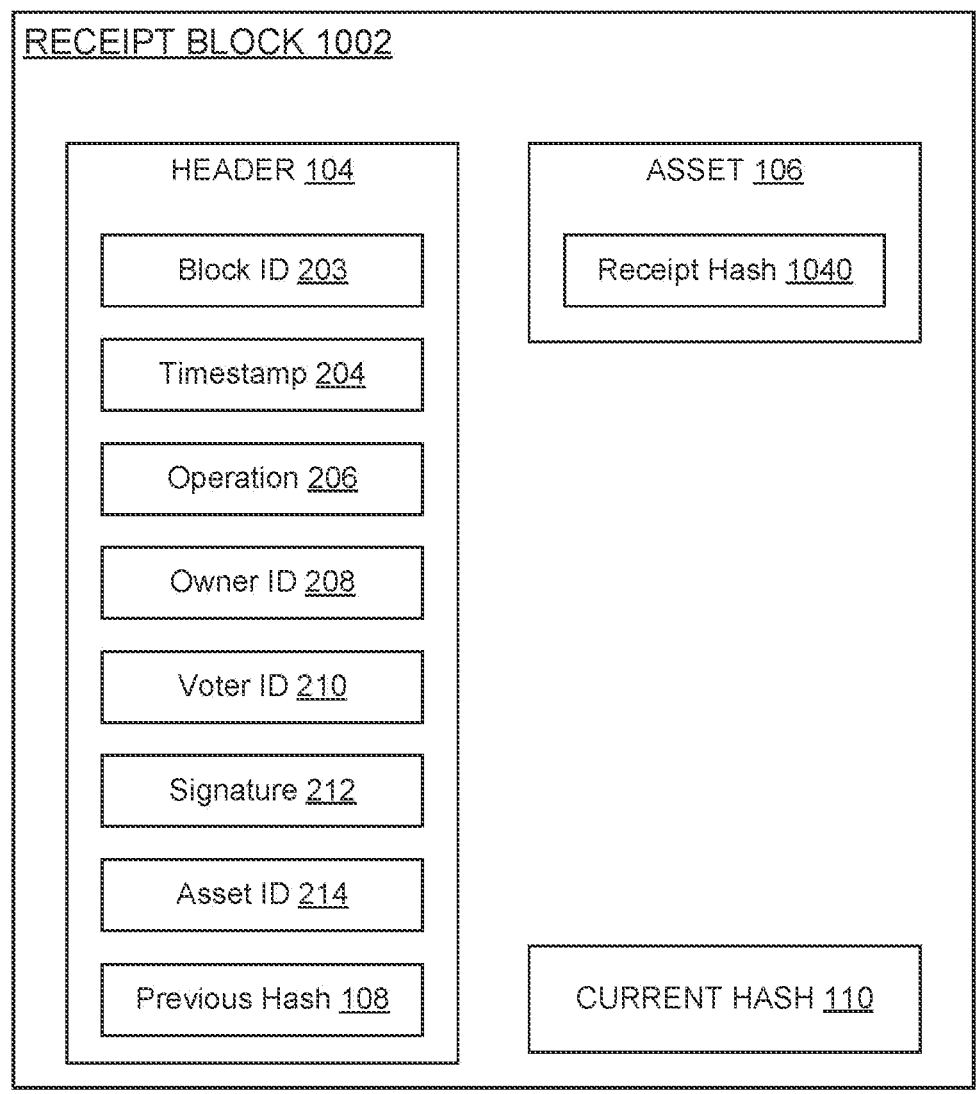
FIG. 10 shows a receipt block that is similar to the data block of FIG. 2 except that it stores a receipt hash value as its asset instead of data, in an embodiment.

FIG. 10 shows a receipt block 1002 that is similar to the data block 202 of FIG. 2 except that it stores a receipt hash value 1040 as its asset 106 instead of data 206. Each consent contract (either owner or global) generates one receipt block 1002 each time it is accessed for a query. The receipt block 1002 is one type of block 102, and thus may be stored in the blockchain 100 similarly to data blocks 202, owner consent blocks 302, and global consent blocks 702. To reduce growth of the blockchain 100, each receipt block 1002 may be alternatively stored in a blockchain separate from the blockchain 100. Receipt blocks 1002 serve as a record of when the blockchain 100 was queried and which of the n blocks 102, in particular, were accessed. Thus, receipt blocks 1002 may be used as part of an audit to verify the integrity of the blockchain 100.

The receipt hash value 1040 may be formed by hashing one or more of: the generating consent contract that generated the receipt block 1002 (e.g., the owner consent contract 300 of FIG. 3, or the global consent contract 700 of FIG. 7), the public identifier of the querying entity, the query (e.g., one or more strings of query commands that define the query), and the asset IDs 214 of the blocks 102 to which the generating consent contract granted permission (e.g., the subset $CC_i$ in Eqn. 1).

Secure Adaptive Data Storage Platform

Figure 11:
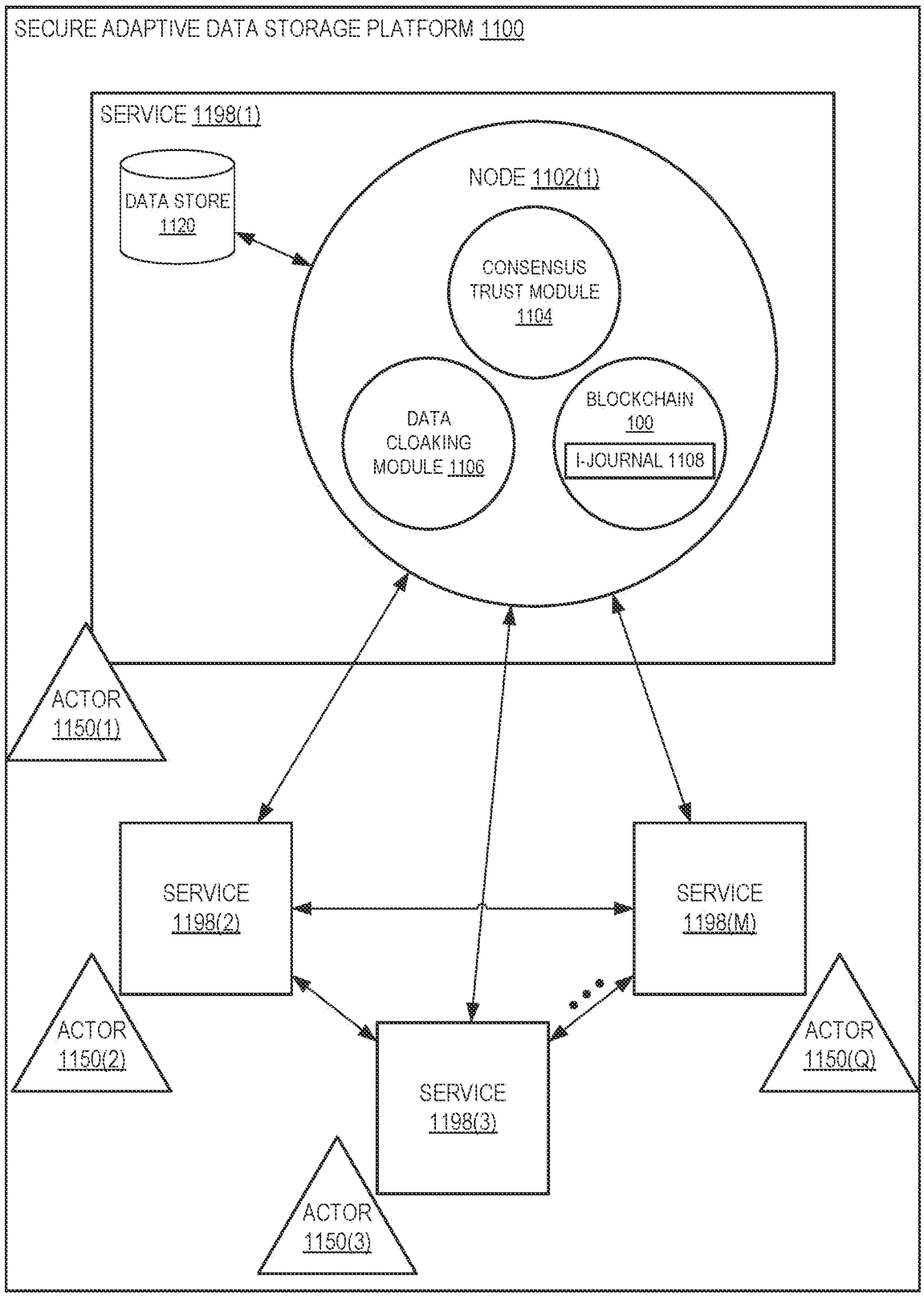
FIG. 11 shows a secure adaptive data storage platform with which the present embodiments may be implemented, in embodiments.

FIG. 11 shows a secure adaptive data storage platform 1100 with which the present embodiments may be implemented. The platform 1100 may be, for example, located in "the cloud" and accessible via a computer network (e.g., the Internet). The platform 1100 includes a plurality of interconnected nodes 1102 that communicate with each other via the computer network. Each node 1102 is a computer that includes at least one processor, a memory (e.g., one or more of RAM, ROM, FLASH, magnetic media, optical media, etc.) and one or more interfaces for communication. Each node 1102 provides a service 1198 to an actor 1150, wherein the services 1198 store data received from one or more of the actors 1150, and make the stored data available to one or more of the actors 1150. The platform 1100 may support swarm intelligence by leveraging a distributed nodal architecture, advanced data security, and machine intelligence. The platform 1100 provides dynamic intelligent data APIs that may drive many analytic approaches and artificial intelligence solutions. By combining various approaches, the platform 1100 provides a distributed learning environment where individual actors contribute specific intelligence and insights but collectively produce a very intelligent "swarm."

Each node 1102 of the platform 1100 has software, formed of machine-readable instructions stored in the memory that, when executed by the processor, control the node 1102 to implement the functionality described herein. Specifically, each node 1102 may include a consensus trust module 1104, a data cloaking module 1106, and an immutable journal 1108 that cooperate to protect data stored within one or more data stores 1120. The consensus trust module 1104 provides the basis for managing trust across all components of the platform 1100. Trust, a central tenant of any secure data system, is managed on a peer-to-peer basis, wherein the nodes 1102 collectively manage trust. The nodes 1102 are connected peer-to-peer (P2P) using a leaderless gossip-based protocol. All communication for the P2P consensus algorithm occur over this protocol via TCP/IP and/or UDP transports. The platform 1100 does not have a central trust management node. Instead, the nodes 1102 work concurrently and in competition with one another to validate access to the data stores 1120. The immutable journal 1108 provides "drill back" technology, with the ability to maintain an associative state between a completed analytic study to the original source data. The immutable journal 1108 may be used to provide a proof of derivation for summary analytics.

The data cloaking modules 1106 increases security of stored data by breaking received data into shards, wherein each shard is placed into a secure ciphered (e.g., encrypted) container, randomly distributed across data stores 1120, and periodically moved between the data stores 1120. The nodes 1102 thereby cooperate to protect sensitive data sets while providing on-the-fly access to the data.

The immutable journal 1108, implemented using the blockchain 100, is distributed across the nodes 1102 to provide a secure record of transactions that cannot be altered. Since the immutable journal 1108 is distributed across all the nodes 1102, the consensus trust module 1104 in each node 1102 is aware of, and may validate, all data transactions, thereby increasing security of access to data within the data stores 1120.

Figure 12:
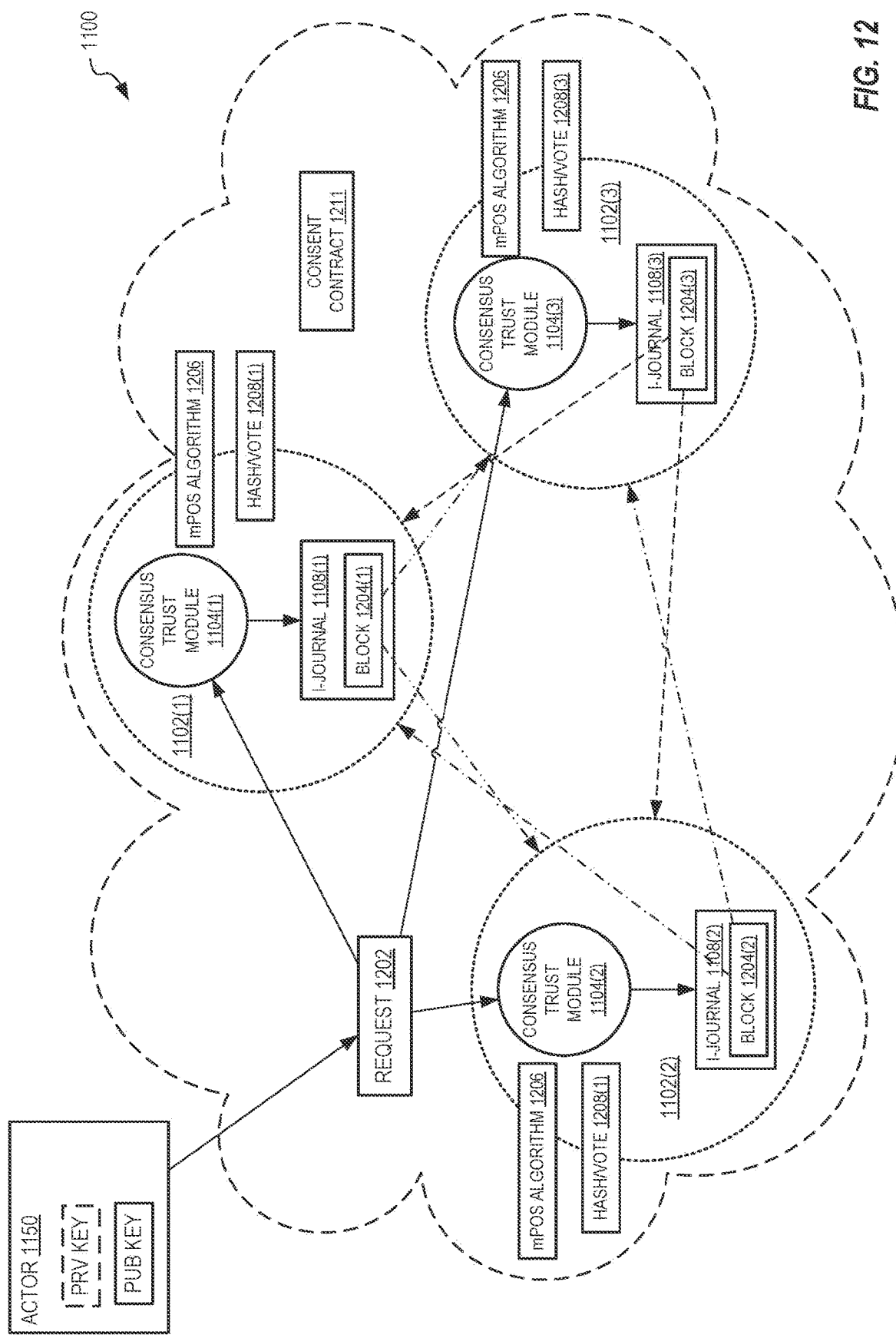
FIG. 12 illustrates how a consensus trust module of the secure adaptive data storage platform of FIG. 11 implements distributed trust, in an embodiment.

FIG. 12 illustrates how the consensus trust module 1104 of FIG. 11 implements distributed trust. To store or access data within the platform 1100, an actor 1150 sends a request 1202 to at least one node 1102. The request 1202 is distributed to all nodes 1102 of the platform 1100, and each node 1102 uses a modified proof-of-stake (mPOS) algorithm 1206 for the request 1202. Within each node 1102, the consensus trust module 1104 uses the mPOS algorithm 1206 to determine a hash/vote 1208 that defines the integrity of the data and integrity of other voters' calculated hash values (e.g., SHA256). Since the voter (e.g., node 1104) is trusted and has a stake in maintaining the integrity of the data for the collective good, it votes on the validity of the data and hash value. The data is updated with the new hash/vote 1208 and other nodes 1102 also collectively vote on the validity of the data until a majority is reached. The mPOS algorithm 1206 and hash/votes 1208 thereby function as a data integrity check for the data and ensure that a proper owner of the data is also identified. In one example of operation, the actor 1150 sends the request 1202 to a node 1102(2), which then distributes the request 1202 to nodes 1102(1) and 1102(3). Concurrently and independently within each node 1102, the consensus trust module 1104 uses the mPOS algorithm 1206 to determine the corresponding hash/vote 1208 (e.g., a one-way hash and vote) based on the request 1202. The consensus trust module 1104 then creates and adds a block 1204 corresponding to the hash/vote 1208 to the immutable journal 1108 after a majority is reached, which is automatically distributed to all other nodes 1102 of the platform 1100. By working in this manner, no single node 1102 determines the trust of the request 1202, and therefore the integrity of the platform 1100 has no single point of failure. As long as an attacker does not have more computing power than half the computing power of all the nodes 1102, security of the platform 1100 is preserved. Thus, no individual (e.g., a surreptitious attacker) can take over ownership of trust within the platform 1100, and there is no single node/computer to hack. Trust is distributed throughout the platform 1100. Only when a majority of the consensus trust modules 1104 agree is the actor 1150 given access to data within the data stores 1120. That is, only when a consensus of trust has been established for the actor 1150 is the request 1202 acted upon by the data cloaking module 1106.

The platform 1100 implements a peer-based authentication method to establish an initial trust relationship. The platform 1100 also monitors use patterns and excludes nodes 1102 that act maliciously.

Figure 13:
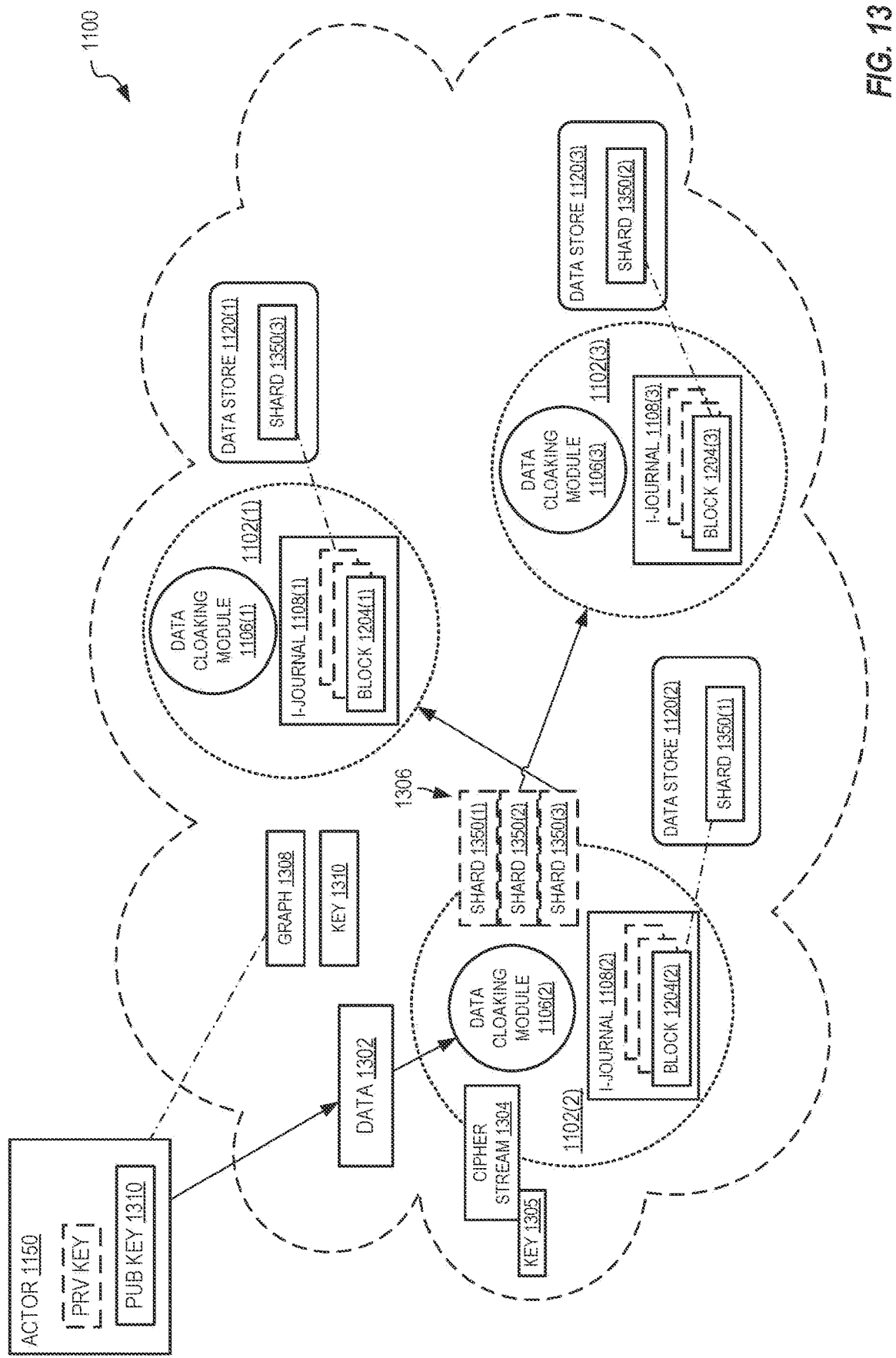
FIG. 13 illustrates how a data cloaking module of the secure adaptive data storage platform of FIG. 11 implements data cloaking, in an embodiment.
Figure 14:
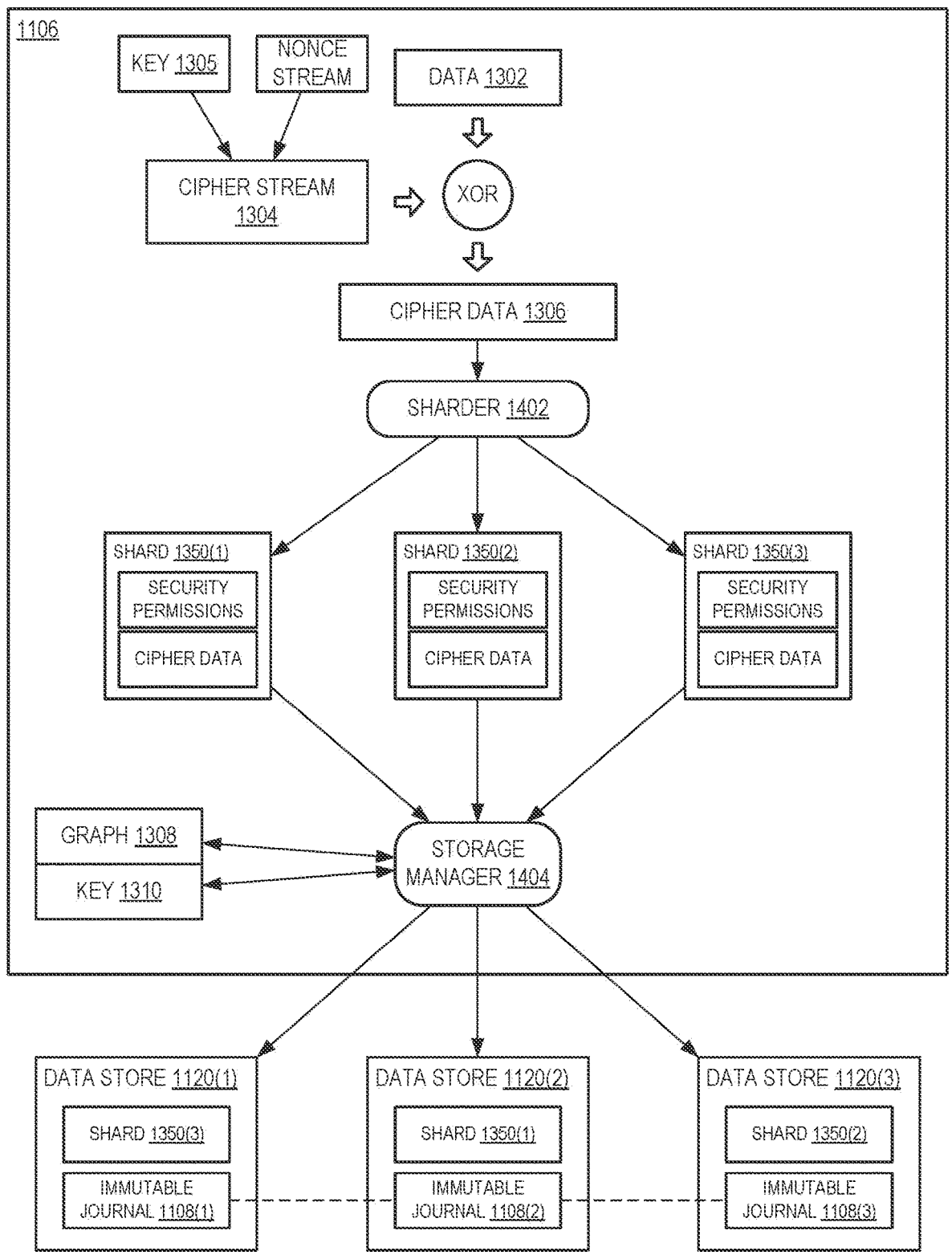
FIG. 14 is a schematic illustrating storage of data by the data cloaking module of FIG. 11, in an embodiment.

FIG. 13 illustrates how the data cloaking module 1106 of FIG. 11 implements data cloaking. FIG. 14 is a schematic illustrating storage of data 1302 by the data cloaking module 1106. FIGS. 13 and 14 are best viewed together with the following description.

Once a consensus of trust has been established for an actor 1150, the actor 1150 sends data 1302 to a node 1102(2) of the secure adaptive data storage platform 1100. The data cloaking module 1106(2) within the node 1102(2) creates a cipher stream 1304 (a type of one-time pad) prior to receiving the data 1302. For example, the cipher stream 1304 can be generated from a nonce stream and a cryptographic key 1310. As the data 1302 is received, and prior to storing and/or transmission within the platform 1100, the data cloaking module 1106(2) ciphers the data 1302 using the cipher stream 1304 to generate cipher data 1306. For example, the data cloaking module 1106(2) may exclusive-OR (XOR) the incoming data 1302 with the cipher stream 1304 to form the cipher data 1306. The cipher stream 1304 is used similarly to decipher the cipher data 1306. This approach allows the platform 1100 to handle large data sets without the typical time and computational resources normally required for cryptographic functions. This may be referred to as vertical data cloaking. The data cloaking module 1106 may implement vertical cloaking using the immutable journal 1108 and one or more keys. For example, keys used for cloaking the data 1302 may be a composite of a hash of previous, current, and subsequent blocks of data in the original clear text stream. These keys may be stored within a data rights management layer of the platform 1100.

The data cloaking module 1106 also implements "horizontal data cloaking" that subdivides the cipher data 1306 into a plurality of subsets that are then shared across multiple nodes 1102. As shown in FIG. 14, data cloaking module 1106 includes a sharder 1402 that divides the cipher data 1306 into a plurality of shards 1350. In certain embodiments, the shards 1350 are of equal size, wherein a final shard 1350 may be null-filled (e.g., padded with zeros) when not entirely filled by the cipher data 1306. The data cloaking module 1106 uses multi-key management to protect each shard 1350 against information loss and to maintain strict access control to each shard 1350. Only permitted parties (e.g., actor 1150) are allowed to access the shards 1350. The shards 1350 that form one particular data set (e.g., the cipher data 1306, and thus the data 1302) may be referred to as an "information set".

Sharding is independent of where the shards 1350 are stored. The shards 1350 may be stored within a traditional RDBMS or NoSQL data store, a global content addressable key space as implemented in DHT, or directly in a blockchain.

For each shard 1350 created from the data 1302, a storage manager 1404 of the data cloaking module 1106 determines at least one data store 1120 for storing the shard, sends that shard to the corresponding node 1102, keeping the shards 1350 that are to be stored locally. For each shard 1350, the data cloaking module 1106 (either the local module 1106 or a receiving module 1106) adds a block 1204 defining the shard and its storage location to the immutable journal 1108. Each block 1204 may also identify the source (e.g., the actor 1150) and structure (e.g., type of data) of the portion of the data 1302 within the associated shard 1350. As shown in FIG. 13, the data cloaking module 1106(2) stores the shard 1350(1) in the local data store 1120(2) and creates the block 1204(2) within the immutable journal 1108(2); the data cloaking module 1106(1) receives the shard 1350(3) from the node 1102(2), stores the shard 1350(3) in the data store 1120(1), and creates the block 1204(1) within the immutable journal 1108(1); and the data cloaking module 1106(3) receives the shard 1350(2) from the node 1102(2), stores the shard 1350(2) in the data store 1120(3), and creates the block 1204(3) within the immutable journal 1108(3).

As described above, the blocks 1204 written to the immutable journal 1108 in one node 1102 are automatically distributed to all of the other nodes 1102. Thus, the immutable journal 1108 contains immutable information as to the location of each shard 1350. The block 1204 within the immutable journal 1108 defines the source and structure of data within its corresponding shard 1350, together with the location of the shard 1350 within the platform 1100.

Periodically, within each node 1102, the storage manager 1404 submits a block 1204 containing a proof of maintenance (POM) to the immutable journal 1108 for each "local" shard 1350 as evidence of maintenance of the local shard at that node. These POM blocks 1204 may be used to determine whether sufficient copies of each shard 1350 are in existence within the platform 1100, and thus whether more copies of the shard 1350 should be created.

Periodically, within each node 1102, the storage manager 1404 randomly selects and sends one or more locally stored shards 1350 to one or more other nodes 1102 for storage, and where the immutable journal 1108 indicates that sufficient copies of each moved shard 1350 are stored within the platform 1100, deletes the local copy of that shard 1350.

Figure 15:
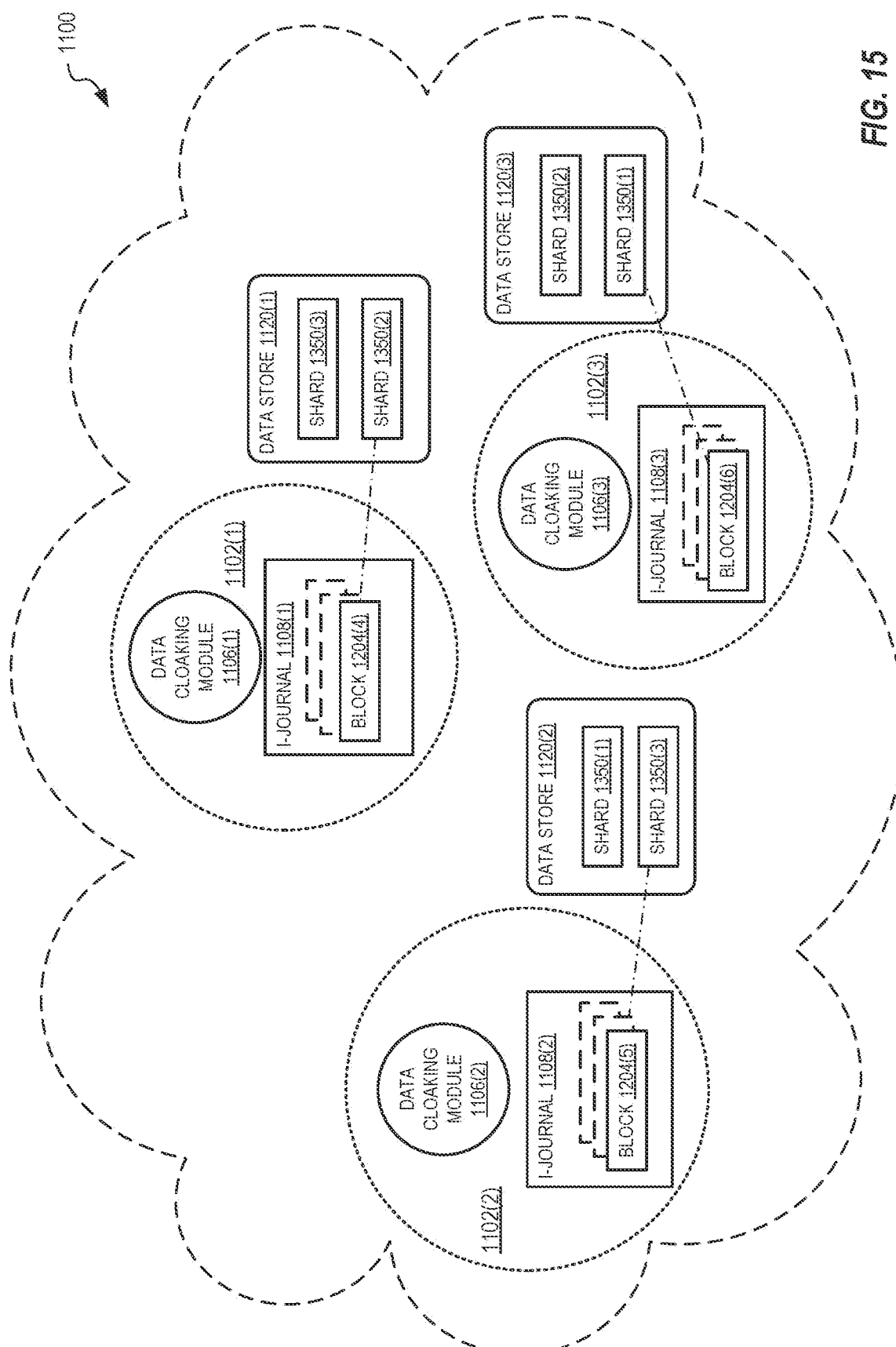
FIG. 15 illustrates a first maintenance step for distributing shards within the secure adaptive data storage platform of FIG. 11, in an embodiment.

FIG. 15 illustrates a first maintenance step for distributing shards 1350 within the secure adaptive data storage platform 1100 of FIG. 11. First, the data cloaking module 1106(1) sends a copy of the shard 1350(3) to the node 1102(2), the data cloaking module 1106(2) sends a copy of the shard 1350(1) to the node 1102(3) and the data cloaking module 1106(3) sends a copy of the shard 1350(2) to the node 1102(1). Second, the data cloaking module 1106(1) generates and stores, within the immutable journal 1108(1), a block 1204(4) corresponding to the shard 1350(2). Third, the data cloaking module 1106(2) generates and stores, within the immutable journal 1108(2), a block 1204(5) corresponding to the shard 1350(3). Fourth, the data cloaking module 1106(3) generates and stores, within the immutable journal 1108(3), a block 1204(6) corresponding to the shard 1350(1). Thus, after this first maintenance step, the shards 350 are further protected through redundancy.

Figure 16:
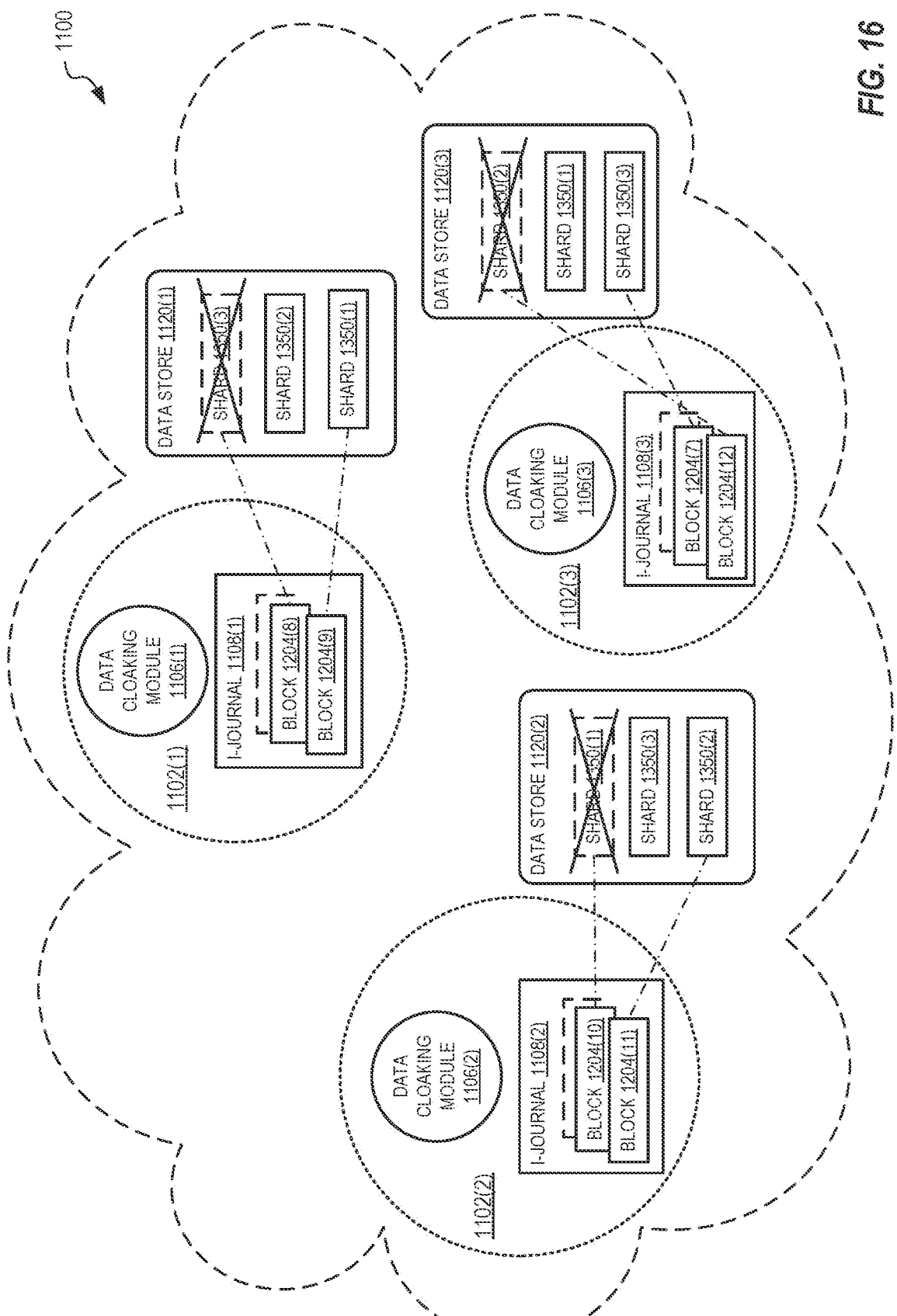
FIG. 16 illustrates a second maintenance step for moving the shards within the secure adaptive data storage platform of FIG. 11, in an embodiment.

FIG. 16 illustrates a second maintenance step for moving shards 1350 within the secure adaptive data storage platform 1100. First, the data cloaking module 1106(1) sends a copy of the shard 1350(3) to the node 1102(3). The data cloaking module 1106(3) generates and stores, within the immutable journal 1108(3), a block 1204(7) corresponding to the shard 1350(3) stored in the data store 1120(3). The data cloaking module 1106(1) then deletes the shard 1350(3) from the data store 1120(1), and generates and stores, within the immutable journal 1108(1), a block 1204(8) corresponding to the deleted shard 1350(3).

Second, the data cloaking module 1106(2) sends a copy of the shard 1350(1) to the node 1102(1). The data cloaking module 1106(1) generates and stores, within the immutable journal 1108(1), a block 1204(9) corresponding to the shard 1350(1) stored in the data store 1120(1). The data cloaking module 1106(2) deletes the shard 1350(1) from the data store 1120(2), and generates and stores, within the immutable journal 1108(2), a block 1204(10) corresponding to the deleted shard 1350(1).

Third, the data cloaking module 1106(3) sends a copy of the shard 1350(2) to the node 1102(2). The data cloaking module 1106(2) generates and stores, within the immutable journal 1108(2), a block 1204(11) corresponding to the shard 1350(2) stored in the data store 1120(2). The data cloaking module 1106(3) deletes the shard 1350(2) from the data store 1120(3), and generates and stores, within the immutable journal 1108(3), a block 1204(12) corresponding to the deleted shard 1350(2).

Thus, the shards 1350 periodically move location within the platform 1100. Since the shards 1350 are not static and are distributed across more than one data store 1120, the "attack profile" for hackers of the stored data is significantly reduced since the data is not in a single location and is constantly moving. This approach also provides "built-in" disaster recovery since the shards 1350 are stored in multiple locations, as shown in FIG. 16, such that catastrophic failure of any one location does not result in data loss. The platform 1100 may include fewer or more nodes 1102 and data stores 1120 without departing from the scope hereof. Shards 1350 may be stored in fewer or more than two locations without departing from the scope hereof.

Figure 17:
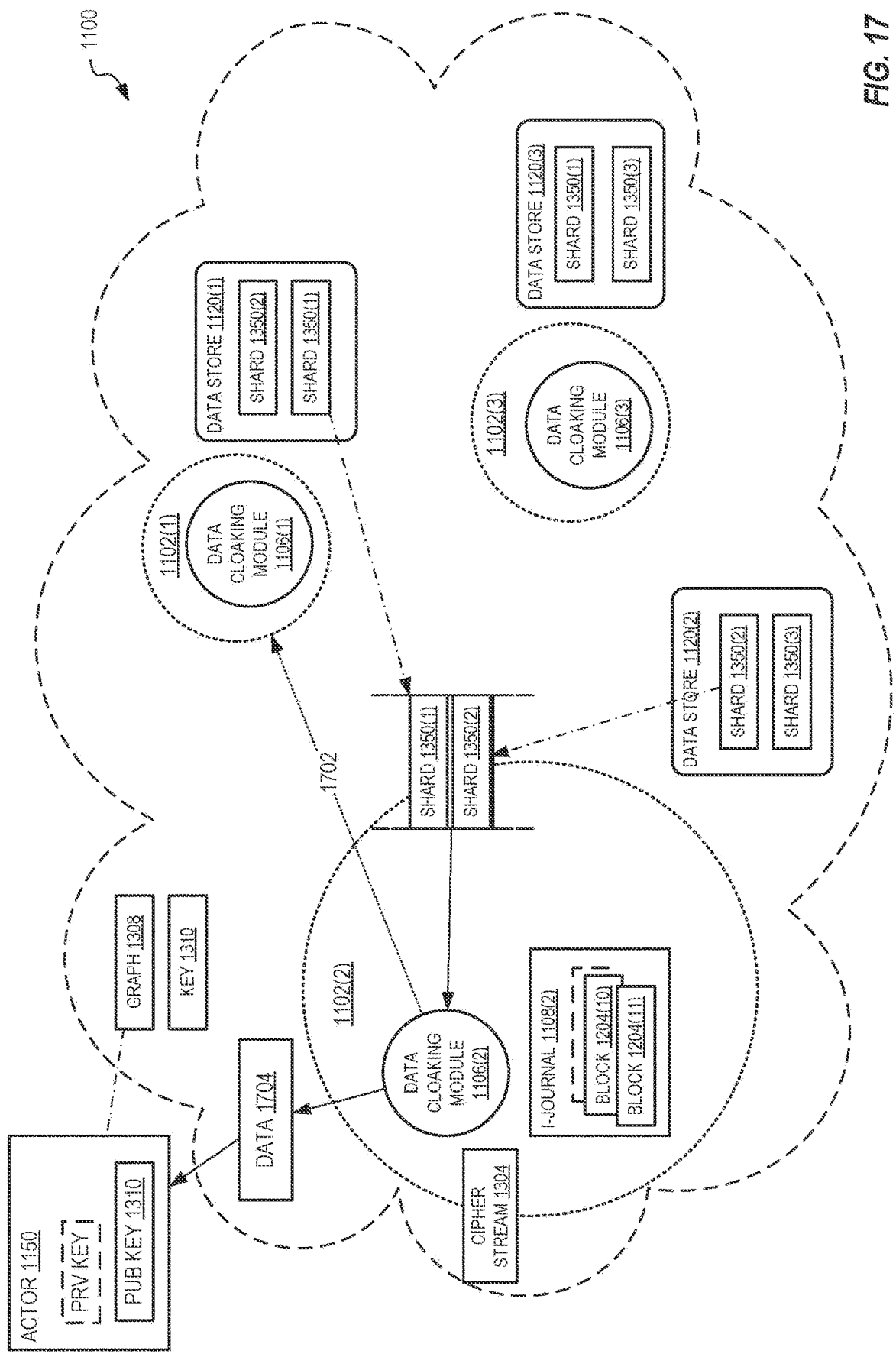
FIG. 17 illustrates how the data cloaking module of FIG. 11 retrieves data, in an embodiment.

FIG. 17 illustrates how the data cloaking module 1106 retrieves data. To access any part or all of the information set (i.e., the data 1302 of FIG. 13), the data cloaking module 1106 searches the immutable journal 1108 for blocks corresponding to the shards 1350 of the data 1302. The data cloaking module 1106 then determines a topology of keys 1310 used to protect the shards 1350, and compares that journal to a graph 1308 that represents the identity of the information requestor. The data cloaking module 1106 then determines a current location (i.e., one or more nodes 1102 and/or data stores 1120) of each shard 1350 needed for the requested data, and then sends a message 1702 to each corresponding node 1102 requesting those shards from the determined locations. Where the data is stored local to the data cloaking module 1106, it is retrieved directly from the corresponding data store 1120. For example, based upon the blocks 1204, the data cloaking module 1106(1) sends the message 1702 to the node 1102(1) requesting the shard 1350(1) from the data store 1120(1), and similarly retrieves the shard 1350(2) from the data store 1120(2). Once the necessary shards 1350 are received, the data cloaking module 1106 uses the appropriate portion of the cipher stream 1304 to decipher the shards 1350 to form data 1704.

One side effect of this approach is that cloaking (e.g., as illustrated in FIGS. 13 and 14) and data retrieval (e.g., as illustrated in FIG. 17) tend to be distributed across the network topology of the platform 1100, thereby avoiding the inadvertent creation of "hot spots" which could impact network performance.

The platform 1100 may provide data input and access layers supporting several interfaces, including one or more of: FHIR, HL7, XML, EDI, X12, JSON, CSV, XLSX, and so on. The platform 1100 may also support multiple transports and/or data sources, including one or more of HTTPS, SFTP, Queue, Stream, IoT, WebSocket, batch, and so on. Data may be received from multiple data sources (e.g., hospitals, labs, patients, radiology, devices, other).

Figure 18:
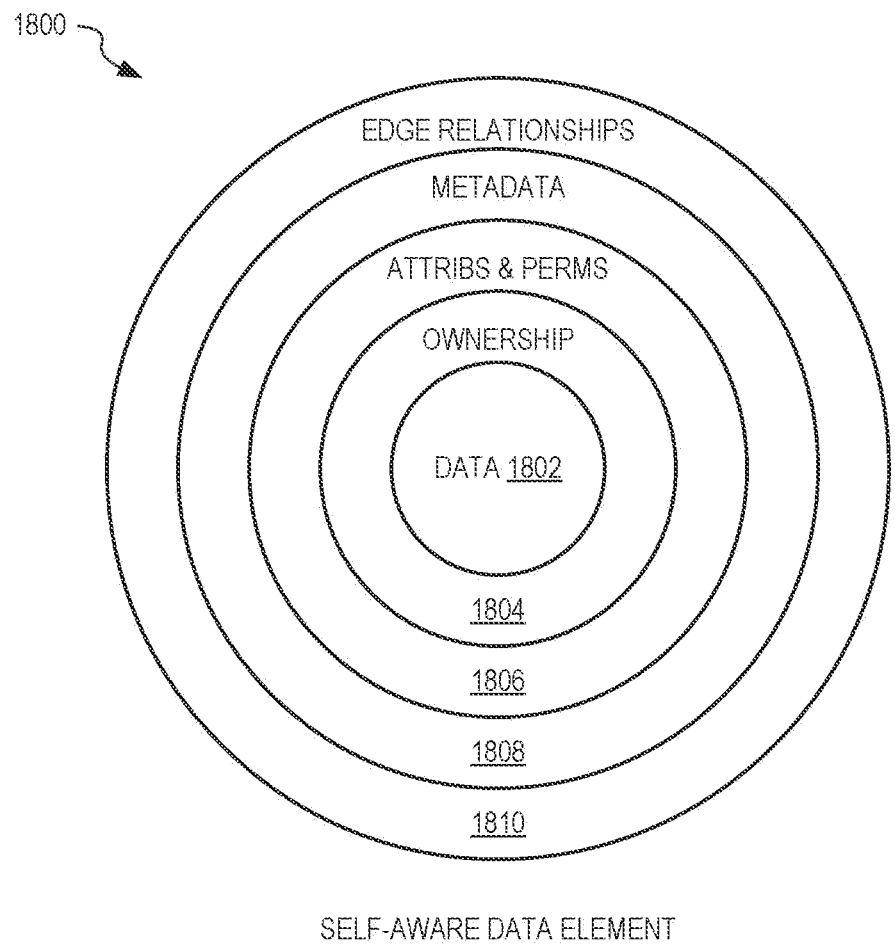
FIG. 18 is a schematic of a self-aware data element, in embodiments.

FIG. 18 is a schematic of a self-aware data element 1800. As data 1802 (e.g., the data 206 of a data block 202 of FIG. 2, or the data 1302 of FIG. 13) is processed, it is converted to a verifiable state by one node 1102 of the platform 1100. The consensus trust module 1104 validates the data 1802 (and additional information stored in the self-aware data element 1800) and gains a voting consensus on the data 1802 from other nodes 1102. Once approved, the data 1802 is promoted to be a verified data set. This allows the data 1802 to be immutable and provable within the context of a complete data set. The self-aware data element 1800 includes the following layers: data 1802 (e.g., data 206 of FIG. 2), ownership information 1804, attributes and permissions 1806, metadata 1808, and edge relationships 1810. The attributes and permissions 1806 may be dynamically derived via consent contracts (e.g., any one or more of the consent contracts 300, 400, 500, 600, 700, and 800). Other than ownership, no other explicit permissions are attached to the self-aware data element 1800.

Usage of the layers of the self-aware data element 1800 vary by use-case. The data 1802 may be used by applications and the end user. The ownership information 1804 may be enforced such that only owners can edit, delete, transfer ownership, and write smart contracts to grant permissions to other users. The attributes and permissions 1806, and the metadata 1808, may include data tags (e.g., key/value pairs) that the data owner can apply to help identify commonalities and descriptions (e.g., tagging several data elements with DATA_TYPE=LAB). The metadata 1808 may also be query-able by users.

The immutable journal 1108 may be implemented as a "Big-Data", NoSQL storage-backed blockchain engine. The immutable journal 1108 allows analytics to be performed on both the data (e.g., data 1302 of FIG. 13) and the block data (e.g., as stored within each asset 106). The platform 1100 combines the block data (e.g., blocks 1204) and the users' data (e.g., data 1302) in the same query-able structure to promote functionality for consent and ownership within a single step. Thus, the implementation of the platform 1100 does not require database administrators to manage multiple data stores for the point of analytics.

The immutable journal 1108 implements a distributed and permissioned blockchain that uses a consensus and voting algorithm to provide better throughput, as compared to conventional blockchain implementations, for data ingestion, thereby solving the low-throughout of prior-art proof-of-work algorithms.

The immutable journal 1108 enforces ownership of the data 1302. Data used for analytics (or transaction) purposes is only available through explicit access of ownership or through explicit access via one or more owner-created consent contracts (e.g., see the owner consent contract 300 of FIG. 3). Each consent contract may be a JSON document that defines Boolean logic for granting or revoking access to corresponding data 1302. Consent contracts give to an individual his/her rights over his/her health information, and set rules and limits on who may look at and receive this information through an informed consent process.

Consent contracts provide the overall data rights management, enforcement, and security for individual data elements and data collections. Data use permissions, security, and value attributes are embedded in the data object itself. The platform 1100 may expose a comprehensive API and management interface to allow data owners to create and manage consent contracts.

The platform 1100 may expose verifiable data sets through the consent layer to the ecosystem layer. The consent layer enforces two types of consent: 1) implicit and 2) explicit. Implicit consent is inherent to the self-aware data element 1800 (a.k.a., verifiable transaction). The autonomous data element has one or more owners that provide the accessor the rights to the data. Additionally, the one or more owners may grant explicit consent to their data elements by way of a consent contract. The consent contract defines the rules (and possible time limitations; see timing rules 306 in the consent contract 300 of FIG. 3) and what data may be accessed by whom. The consent layer enforces both consent types upon all data access requests.

The platform 1100 provides the ability to identify and protect an individual's identity across multiple repositories. By doing this, the individual can access their information, provide consent for others to see and use their information, and receive notifications when their information is accessed. This data access layer can enable a whole new generation of personal and precision health applications highly tailored to the individual.

The ecosystems layer contains subscription-based solutions and data domains. These solutions may range in complexity from a data processing that manages complex business logic for other applications, to a fully formed front-end UI that provides a full stack application using protocols of the platform 1100. The platform 1100 provides a visualization and intelligence aggregation capability for users.

The ecosystem creator may define the economic contracts for reselling their applications to other entities without dealing with the issues of platforms, databases, connectivity, etc. and just focus on the business solution they provide. The fee model and business models may vary from application to application as dictated by the ecosystem creator.

The ecosystem may leverage the dynamic definition of data domains, so that consented verified transactions are used. These data elements may be used in a variety of Big Data and Deep Learning algorithms to support the business needs. The ecosystem may use NoSQL and graph databases for data exploration and exploitation.

The immutability of the data 1302 is also enforced. However, there are mechanisms for transferring and updating data after creation, albeit only by the owner. The update and transfer operations against a block (e.g., the data block 202 of FIG. 2) result in a new block 1204 in the immutable journal 1108. However, the self-aware data element 1800 contains identifiers for previous versions of the block. When a query is performed, only the current version of a block is query-able. However, once a block is identified, the user may request to see all previous operations on that block (which is the audit trail).

Smart contracts may be written with the intent of creating new data, transferring data, and updating data. Another distinction provided by the platform 1100 is the ability for the application to update data without violating immutability. The immutable journal 1108 also allows for implicit access and rights to the self-aware data elements 1800 through ownership. The immutable journal 1108 does not implement access and rights using a separate table or database, as done in the prior art. Rather, the platform 1100 provides access and rights through self-aware data elements 1800. Through the data hiding capabilities of the platform 1100, the blockchain 100 is secured through multiple means, thereby keeping the data 1302 safe, immutable, provable, and auditable.

In one embodiment, the platform 1100 uses four types of smart contract: (1) Asset Creation: may produce another asset (e.g., data) as part of its execution. For example, the smart contract may add another asset (data) that documents fulfillment of an order (transaction). (2) Asset Transfer: may dictate that the asset identified by the smart contract is to be transferred to another entity. (3) Consent: may return a value to allow the requestor access or not to the asset. (4) General: may run the requested smart contract and perform steps defined in the contract.

The platform 1100 may use one of several different modes for invoking the smart contract: (1) On-creation: steps of the smart contract are performed on any new block/data being created. (2) On-demand: the smart contract is invoked upon a user request (against one or many blocks). Smart contacts may use NoSQL database tools, such as TQLFlow and TQL, for on-demand execution. (3) On-event: the smart contract is invoked by an event (e.g., a timer). For example, an escrow smart contract may be invoked when two or more parties have fulfilled their agreed upon actions to release the corresponding asset to the previously agreed upon entity. (4) On-access: the smart contract is invoked when access to the corresponding asset is requested and operates to grant the access to someone other than the owner(s). Reserved specifically for consent contracts.

By default, the immutable journal 1108 stores assets (e.g., data 1302 in FIG. 13, or asset 106 in FIGS. 1-3) as structured or unstructured data (e.g., as defined by the chain administrator and/or creator of the asset). The platform 1100 and immutable journal 1108 may also allow an application developer or chain administrator to define a non-structured, a semi-structured, or a fully-structured asset 106. The immutable journal 1108 performs validation on the asset at creation time to ensure that the asset adheres to the nom-, semi- or fully-structured definition. Data types are also enforceable, and basic normalization of data types occurs. The structures may be complex and contain nested objects. Finally, the definition of the asset may contain indexes, which are created to aid in queries.

When the immutable journal 1108 is implemented as a NoSQL engine, the ability to horizontally scale storage and query performance is close to a NoSQL engine. The protocol used by the immutable journal 1108 does add necessary overhead for block creation and management while managing verifiable data sets. However, the tradeoff is the ability to scale out to tera- or peta-bytes of data. Scaling within prior-art blockchain implementations has already experienced issues.

With the features of a NoSQL engine and unstructured data (or semi- to fully-structured data) the ability for full normalization is not necessary. Schema-on-read is used to apply additional structure or relationship upon the query (or read) of the data. This eliminates the costly need of Extract-Transfer-Load (ETL) or structuring data for analytics (and the costly steps of restructuring data when the requirements of the analytics change). It is here that the immutable journal 1108 may seamlessly integrate the data of a chain(s) into a graph for the purposes of expanding the analytic capability of the data.

Various protocols have been and are being developed which have distinctions that are advantageous to the use-case or problem set at hand and then there are some features that are detractors. The immutable journal 1108 was created to address the needs of healthcare and data security while leveraging the benefits of blockchain and Big Data analytics. The immutable journal 1108 unlocks the data in ways that traditional blockchain and databases cannot achieve.

Advantageously, the platform 1100 unites disparate structured and unstructured data sets from different vendors in one view. The platform 1100 may thereby connect and safely use unlimited data sources, such as one or more of: EMR, revenue cycle, Facebook, demographics and more.

Figure 19:
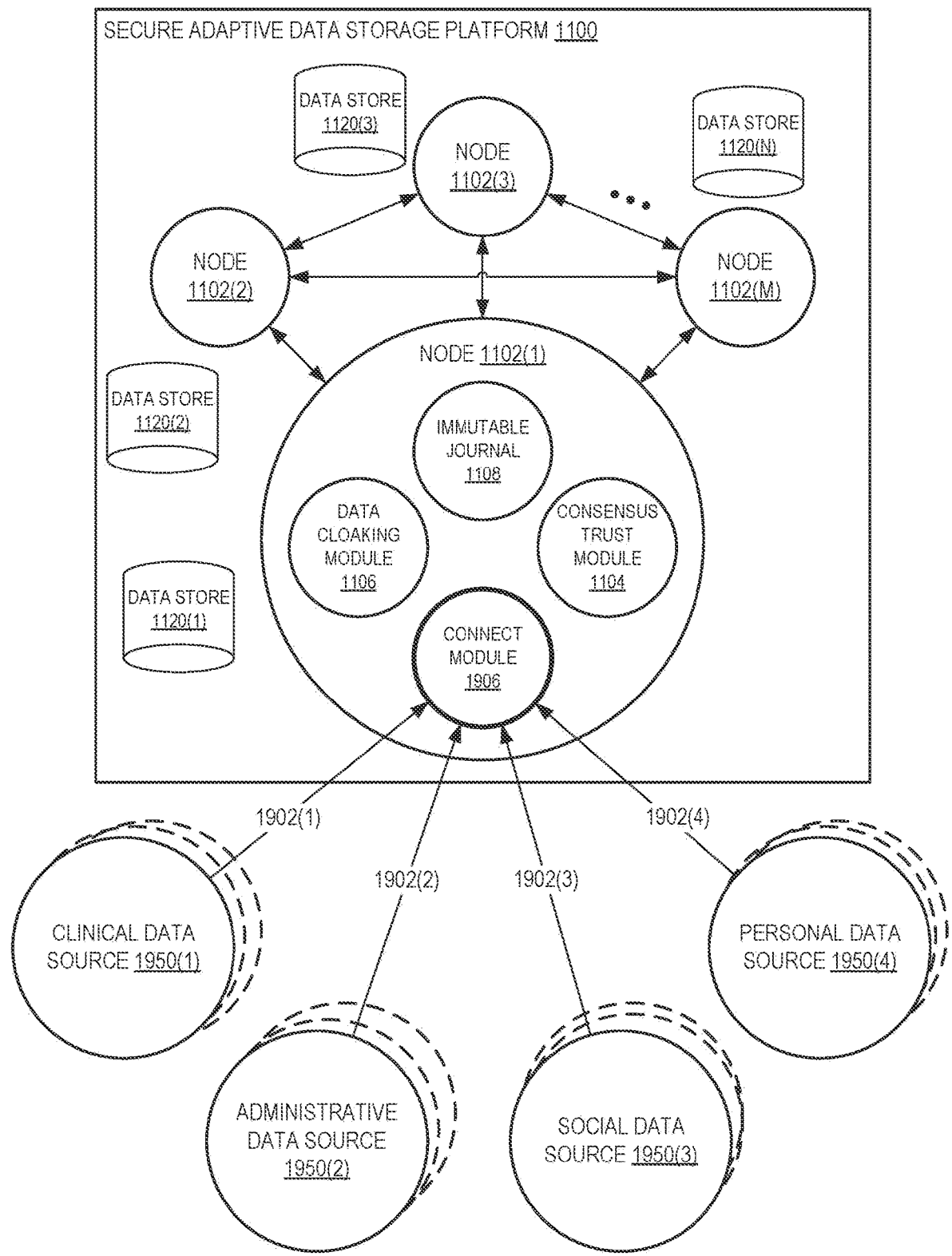
FIG. 19 shows the secure adaptive data storage platform of FIG. 11 using a connect module to collect disparate structured and unstructured data, in an embodiment.

FIG. 19 shows the secure adaptive data storage platform 1100 of FIG. 11 using a connect module 1906 within the node 1102(1) to collect disparate structured and unstructured data 1902. The connect module 1906 may operate in any one or more of the nodes 1102 to collect the data 1902 for storage within the platform 1100. The connect module 1906 may collect data in many different formats, including FHIR, JSON, CSV, Excel, EDI, XML using a batch file interface, REST end points, sockets, and/or other transports. In FIG. 19, the data 1902(1) is collected from a clinical data source 1950(1), the data 1902(2) is collected from an administrative data source 1950(2), the data 1902(3) is collected from a social data source 1950(3), and the data 902(4) is collected from a personal data source 1950(4). The connect module 1906 may accept queueing technologies for streaming data ingestion and enforces the non-, semi-, or fully-structured data objects (as discussed above). The connect module 1906 may also perform basic normalization for data typing. For example, the connect module 1906 may ensure that dates and numerical values are properly typed and stored (especially when originating from streamed-based protocols). For data elements to be queried properly, their data types should be standardized (structure may be done as part of schema-on-read).

The connect module 1906 provides connectivity to other sources and consumers of information. This connectivity ranges from a simple integration with a legacy relational database, up to cloud-scale interactions supporting medical field research across a global network of measurement devices (e.g., a global wearable device info-grid).

As shown, the connect module 1906 supports four key types of integration: clinical, administrative, social, and personal. Thus, the platform 1100 supports deep integration and analytics with clinical systems, and the ability to support the diversity and depth of data inherent in these systems. The platform 1100 also supports connectivity and interoperability with key administrative systems that process and manage the "back office" of providers and payers, reducing uncollectables and improving profitability of providers. The platform 1100 also supports information streams from popular social media (e.g., Twitter, Facebook, etc.), as well as personal connectivity into the growing swarm of wearable/embeddable health technology already available in the market place.

Figure 20:
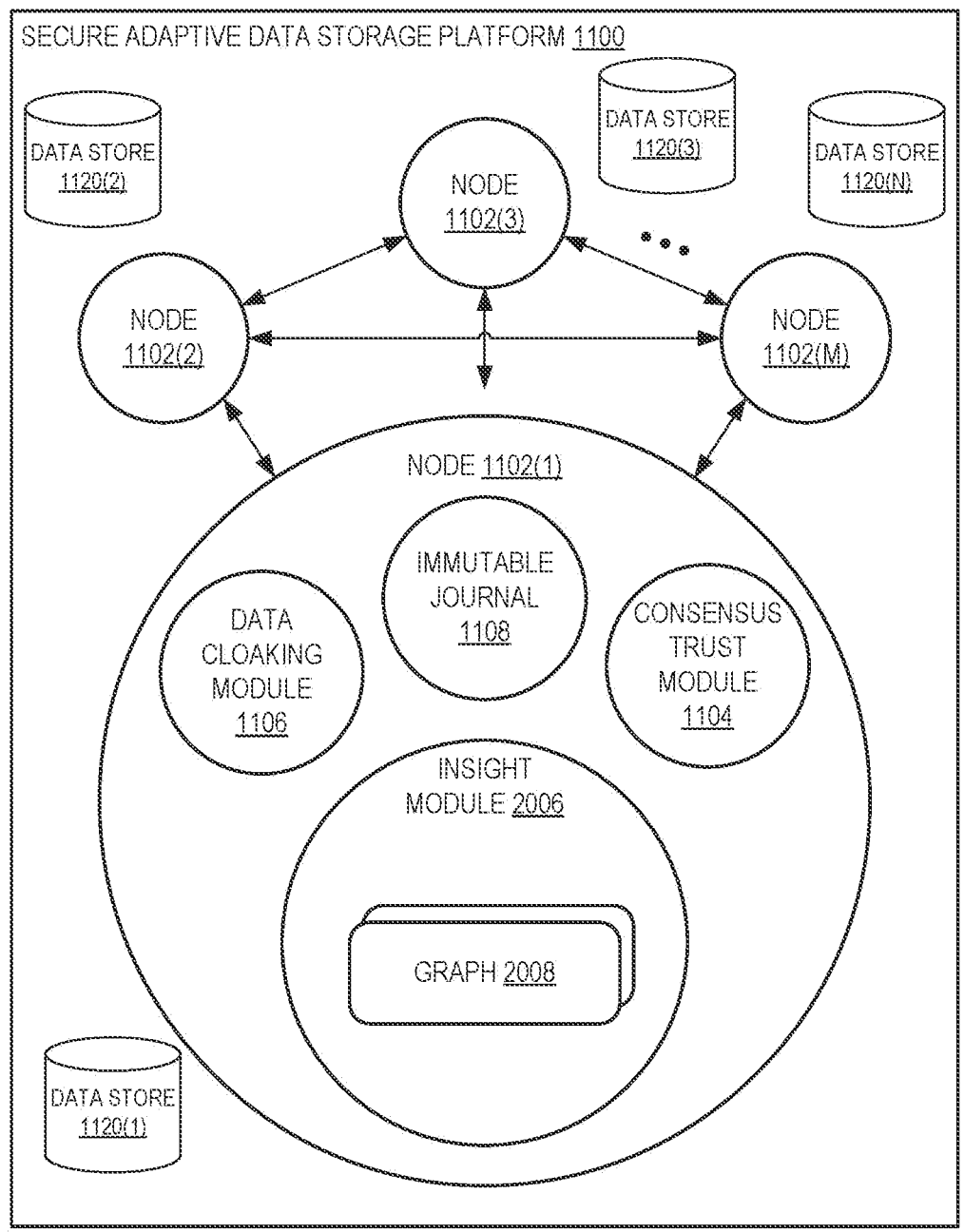
FIG. 20 shows the secure adaptive data storage platform of FIG. 11 using an insight module to generate one or more graphs of data stored within the platform, in an embodiment.

FIG. 20 shows the secure adaptive data storage platform 1100 of FIG. 11 using an insight module 2006 within the node 1102(1) to generate one or more graphs 2008 of data stored within the platform 1100. The insight module 2006 may be implemented within two or more nodes 1102 of the platform 1100 that collectively operate together to provide the functionality of the insight module 2006 as described herein.

The insight module 2006 uses one or more of the consensus trust module 1104, data cloaking module 1106, and immutable journal 1108 to retrieve data from the platform 1100 and to generate the graph 2008 containing that data. The insight module 2006 may include machine-learning algorithms that operate at a cloud scale and with transactional speed. It is known that looking at a slice of data without context limits insight into that data, which is akin to seeing only the dots on a canvas. The insight module 2006 generates the graph 2008 by adding data sources and using a variety of analytic techniques to provide a richer, more complete, and contextualized image of that data.

The insight module 2006 provides the basis of the analytics provided by the platform 1100. The insight module 2006 is designed to process streams of information, setting the stage for rapid adoption of digital health. A Distributed Commit Log (DCL) underlies the foundation for the Insight log. The insight module 2006 allows the platform 1100 to horizontally scale the data rapidly collected by the connect module 1906 of FIG. 19.

The insight module 2006 operates in each node 1102 to provide a real time distributed computation "engine." Any number of transformational grammars may be constructed on the fly and applied in parallel to these data streams, to create derivative streams that provide continuous insight (analytic answers) to multiple simultaneous downstream applications and network services.

In one example of operation, consider the following problem: for a large population of individuals use some form of wearable device (e.g., a fitness tracker) that collects heart and respiration information, collect and analyze the data to provide care for those individuals. The solution can be realized by the platform 1100, where the connect module 1906 is used to receive a continuous high-velocity stream of information from the wearable devices, and where the insight module 2006 analyzes that data to generate one or more graphs 2008 that may be pushed to downstream constituents, where the stream of analytic recommendations contained within the graphs 2008 may be subsequently used to provide "just-in-time" care of the individuals through the most cost-effective delivery means available.

The insight module 2006 may be based on a "Schema-on-Read" design, and highly leverages graph theory as its underlying data access layer. This coupling provides a number of advantages over prior art relational database oriented approaches that spend a lot of time and resources on defining a priori logical and physical schema to handle a finite set of business use cases. While this approach has traditionally worked well, it does not meet the demands of big and sparse data, and thereby limits the ability to distribute intelligence, insight and decision making across the cloud.

The platform 1100 uses graph theory to support the distribution of information across a dynamic computing technology, while supporting a dynamic working set of information. The traditional schema of prior-art database solutions is meaningless within the platform 1100. The platform 1100 uses a set of dynamic data structures that are more readily adaptable to shifting business needs, thereby cutting costs in data modeling and database design. For example, health information is both sparse and dynamic. A health record for one individual may have a very different set of attributes as compared to a health record for another individual. Further, each health record changes over time, both as each individual's needs change and as healthcare itself changes. Prior-art relational models prove to be a challenging approach when dealing such "sparse and dirty data."

Within the platform 1100, the insight module 2006 creates the graph 2008 formed of interconnected "nodes", where nodes represent data (e.g., patients, health provider encounters, drugs, prescriptions, procedures, etc.) and the interconnections between the nodes represent relationships (e.g., patient "Fred" is prescribed Lisinopril). Both nodes and relationships are dynamic, being created and discarded as data is processed.

Since the insight module 2006 uses the graph 2008 to efficiently manage a complex set of relationships between data items, as compared to prior-art relational databases, the platform 1100 avoids maintaining and traversing "join tables" (a standard design approach used to represent relationships in a traditional relational databases) and thereby provides a major performance increase to dramatically expand the types of analysis that be performed. Additionally, by using graph theory, the insight module 2006 processes queries much more efficiently; instead of "joining" the entire data set/table, the insight module 2006 only traverses the relevant sub-graph.

The platform 1100 allows insight into data to be converted into one or more actions using prescriptive analytics models that adapt to behavior patterns. The platform 1100 allows behavior patterns that are constantly changing in small and large ways to instigate meaningful change. Within the platform 1100, intelligent models learn the why, how, when, and where behaviors may change to prompt optimal engagement.

Figure 21:
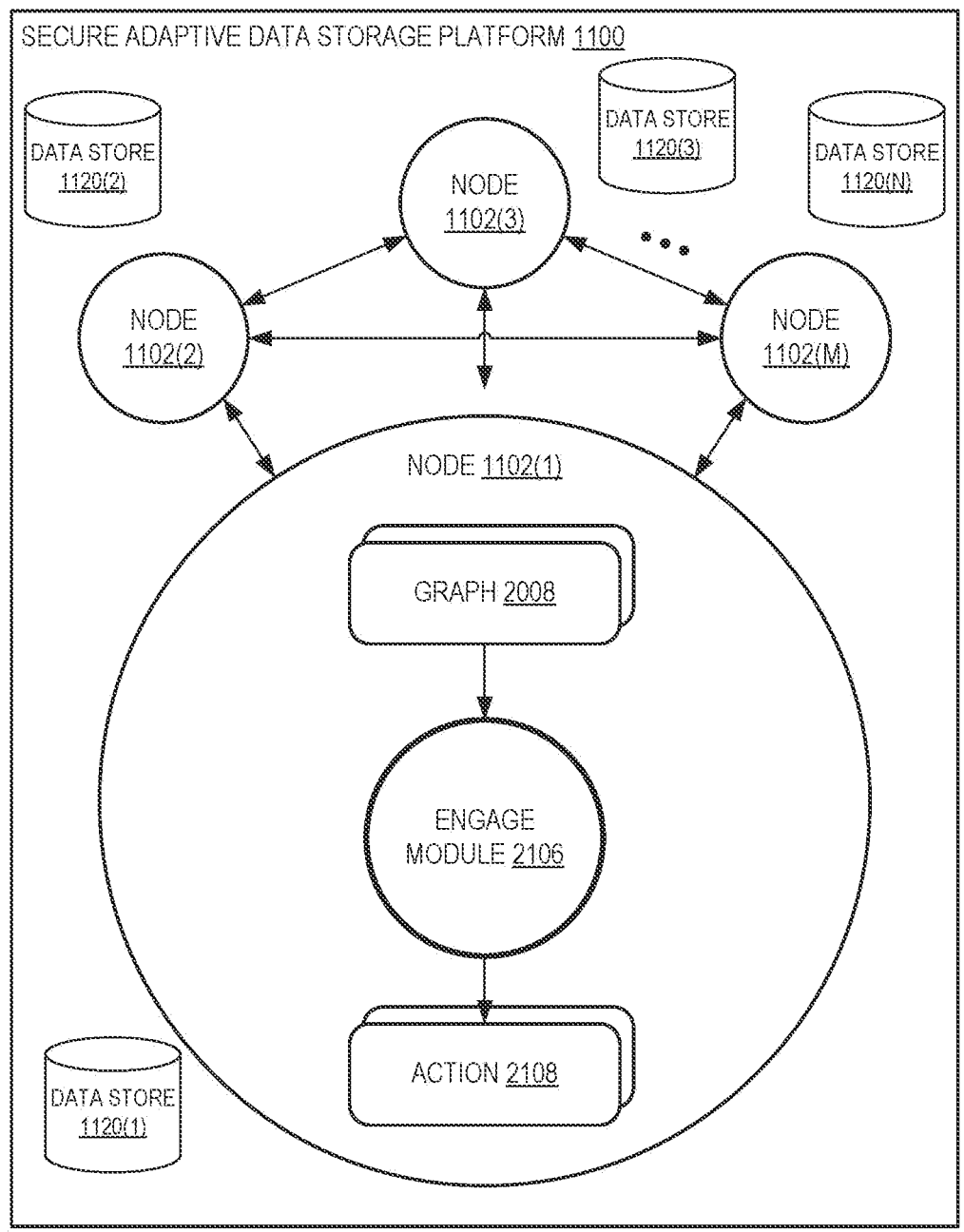
FIG. 21 shows the secure adaptive data storage platform using an engage module to interpret the one or more graphs of FIG. 20 and generate one or more actions, in an embodiment.

FIG. 21 shows the secure adaptive data storage platform 1100 using an engage module 2106 within the node 1102(1) to interpret the graph 2008 and generate one or more actions 2108. The engage module 2106 may be implemented within two or more nodes 1102 of the platform 1100 that collectively operate together to provide the functionality described herein. The engage module 2106 implements one or more prescriptive analytics models to interpret the one or more graphs 2008 and generate human-centric action 2108. The action 2108 may take one of three forms.

First, the action 2108 may provide a wide variety of traditional key performance indicators (KPIs), for example to solve a variety of asset utilization problems. While other systems may provide similar capability, the platform 1100 and engage module 2106 also provide a dynamic environment to apply a variety of "templates" for the creation of various predicative models including decision trees, logistic regression, neural networks, K-nearest neighbor, distance functions, Bayesian, and other numerical analysis methods.

Second, the engage module 2106 may integrate with a wide variety of "eventing" platforms (e.g., event calendaring, collaboration, etc.) to allow users to form ad hoc mechanisms to drive behavior of digital health. This mechanism allows the engage module 2106 to create higher level capabilities, allowing providers to subtly shift the demand preference for services towards more cost-efficient provider platforms (e.g., imaging clinics). For example, the platform 1100 and engage module 2106 may "sense" the preferred mode of dialog with a particular patient (e.g., email, live person, social media messaging, etc.), and present back through the preferred mode a set of cost-effective options for elective diagnostic imaging.

Third, the engage module 2106 uses the immutable journal 1108 as an underlying security mechanism. By creating a set of one-way hashes that authenticate back to common healthcare transactions (e.g., office consultation) and recording them within the immutable journal 1108, the platform 1100 creates a foundation for an entirely new ecosystem for value-based care. This model may have certain advantages:

Adoption Acceleration—New types of services, such as telemedicine, could be more readily adopted by providing a built-in platform for provider reimbursement, breaking the current payer choke-hold.

Float—Crypto money allows providers to be paid immediately upon providing service. No more waiting days/weeks/months for payment.

Anonymity—Just like BitCoin, the patient-provider relationship remains completely anonymous.

Applications

Although applications are not part of the internals of the verified data set (VDS), they are the main consumer of those VDSs. Application developers may build directly on the platform 1100 using a variety of protocols (e.g., web services, streaming data transfer, bulk flat-file ingestion, etc.). Ecosystems have a distinct use-case as previously discussed. The application stack may even be deployed and managed within the platform 1100. The applications may make direct use of the VDSs and/or access ecosystems for data that enhances and supports their applications.

Application developers may leverage the platform-as-a-service and gain all the functionality described so far with little knowledge of databases, security, access or blockchain. In fact, armed with the knowledge of REST, JSON, and Boolean logic, the application developer may create an application with security, ownership, consent, and analytics without the hassle and worry of those pieces, and thereby focus on delivering the next healthcare changing solution. Where equipped with some knowledge of BI and data analytics, the data becomes alive with even greater power. The application developer may finally leverage data science to unlock its full potential.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A blockchain access method, comprising:
    searching, in response to a request from an entity, a blockchain formed from a series of blocks, each of the blocks storing an asset and having an owner, to identify:
        (i) at least one owner consent contract containing one or more owner-specified access rules that determine access for the entity to a portion of an asset that is stored in another block of the blockchain and owned by the owner of the at least one owner consent contract; and
        (ii) at least one global consent contract containing one or more global access rules that determine access for the entity to the portion of the asset;
    querying the blockchain, based on the one or more owner-specified access rules and the one or more global access rules, to identify a plurality of allowed blocks, of the blockchain, containing assets that the entity may access; and
    retrieving, for each of the allowed blocks, a portion of the asset stored therein.

2. The blockchain access method of claim 1, wherein the portion of the asset consists of the entire asset.

3. The blockchain access method of claim 1, the one or more owner-specified access rules including a public identifier that identifies the entity.

4. The blockchain access method of claim 1, wherein the one or more global access rules supersede the one or more owner-specified access rules.

5. The blockchain access method of claim 1, wherein the one or more global access rules are superseded by the one or more owner-specified access rules.

6. The blockchain access method of claim 1, wherein:
    the at least one owner consent contract includes an updated owner consent contract containing one or more updated owner-specified access rules that replace the one or more owner-specified access rules; and
    said querying the blockchain is based on the one or more updated owner-specified access rules instead of the one or more owner-specified access rules.

7. The blockchain access method of claim 1, further comprising outputting the portion of the asset.

* * * * *